United States Patent
Simpson

(10) Patent No.: US 11,076,920 B2
(45) Date of Patent: Aug. 3, 2021

(54) INSTRUMENTATION AND SURGICAL METHOD FOR IMAGE-GUIDED MICROENDOSCOPIC DECOMPRESSION

(71) Applicant: Microendoscopic Spine Institute, LLC, Dallas, TX (US)

(72) Inventor: Andrew K. Simpson, Boston, MA (US)

(73) Assignee: Microendoscopic Spine Institute, LLC, Dallas, TX (US)

(*) Notice: Subject to any disclaimer, the term of this patent is extended or adjusted under 35 U.S.C. 154(b) by 337 days.

(21) Appl. No.: 16/051,692

(22) Filed: Aug. 1, 2018

(65) Prior Publication Data
US 2019/0216546 A1  Jul. 18, 2019

Related U.S. Application Data

(60) Provisional application No. 62/617,975, filed on Jan. 16, 2018.

(51) Int. Cl.
*A61B 1/015* (2006.01)
*A61B 1/313* (2006.01)
(Continued)

(52) U.S. Cl.
CPC .......... *A61B 34/20* (2016.02); *A61B 1/00094* (2013.01); *A61B 1/00096* (2013.01);
(Continued)

(58) Field of Classification Search
CPC .............. A61M 29/00; A61B 1/00094; A61B 1/00096; A61B 1/015; A61B 1/018;
(Continued)

(56) References Cited

U.S. PATENT DOCUMENTS 5,313,934 A * 5/1994 Wiita ................. A61B 1/00091
600/109
5,575,756 A * 11/1996 Karasawa .......... A61B 1/00068
600/121
(Continued)

FOREIGN PATENT DOCUMENTS

EP    1868490 A2    9/2006

OTHER PUBLICATIONS

Wagner et al., Minimally invasive fully endoscopic two-level posterior cervical foraminotomy: technical note; Journal of Spine Surgery; https://www.ncbi.nlm.nih.gov/pmc/articles/PMC5506297/; 2017; 5 pgs.
(Continued)

*Primary Examiner* — Marcela I. Shirsat

(57) ABSTRACT

Instrumentation for microendoscopic surgery comprises a retractor system including a navigated initial probe, nested retractors and a navigated final tubular retractor defining an interior passage extending between a proximal end and a distal working end. A multi-planar navigation marker including a plurality of spaced-apart, radiopaque marker bodies can be mounted to the tubular retractor at a predetermined multi-planar spatial and rotational relation to the distal working end. The retractor can optionally include systems for fluid irrigation and suction with differential activation allows for the option of maintaining a dry surgical field or a submerged surgical field depending on the surgeon's preference during various portions of the procedure. The instrumentation can also include a camera for direct viewing and navigated burrs and/or navigated osteotomes, which allow the surgeon to use direct visualization and/or information from instrument localization on multi-planar images depending on surgeon facility resources.

17 Claims, 21 Drawing Sheets

(51) Int. Cl.
| | |
|---|---|
| A61B 17/02 | (2006.01) |
| A61B 17/17 | (2006.01) |
| A61M 29/00 | (2006.01) |
| A61B 1/00 | (2006.01) |
| A61B 1/018 | (2006.01) |
| A61B 90/00 | (2016.01) |
| A61B 17/00 | (2006.01) |
| A61B 34/20 | (2016.01) |
| A61B 1/05 | (2006.01) |
| A61B 17/16 | (2006.01) |
| A61B 17/34 | (2006.01) |
| A61B 1/07 | (2006.01) |
| A61B 5/06 | (2006.01) |
| A61B 90/30 | (2016.01) |
| A61B 17/32 | (2006.01) |
| A61B 90/57 | (2016.01) |

(52) U.S. Cl.
CPC .............. *A61B 1/015* (2013.01); *A61B 1/018* (2013.01); *A61B 1/05* (2013.01); *A61B 1/07* (2013.01); *A61B 1/3135* (2013.01); *A61B 5/065* (2013.01); *A61B 17/0218* (2013.01); *A61B 17/1671* (2013.01); *A61B 17/1703* (2013.01); *A61B 17/1757* (2013.01); *A61B 17/3417* (2013.01); *A61B 17/3421* (2013.01); *A61M 29/00* (2013.01); *A61B 17/32002* (2013.01); *A61B 90/30* (2016.02); *A61B 90/361* (2016.02); *A61B 90/57* (2016.02); *A61B 2017/0092* (2013.01); *A61B 2017/00345* (2013.01); *A61B 2017/00991* (2013.01); *A61B 2017/3445* (2013.01); *A61B 2034/2057* (2016.02); *A61B 2034/2068* (2016.02); *A61B 2034/2072* (2016.02); *A61B 2090/036* (2016.02); *A61B 2090/3966* (2016.02); *A61B 2090/3983* (2016.02); *A61B 2217/005* (2013.01); *A61B 2217/007* (2013.01)

(58) Field of Classification Search
CPC ..... A61B 1/05; A61B 1/3135; A61B 17/0218; A61B 17/1703; A61B 17/1757; A61B 17/3417; A61B 17/3421; A61B 2017/3445; A61B 2090/3966; A61B 2090/3983; A61B 2217/005; A61B 2217/007

USPC ................................. 600/201, 114, 121, 210
See application file for complete search history.

(56) References Cited

U.S. PATENT DOCUMENTS

| | | | | |
|---|---|---|---|---|
| 6,110,103 | A * | 8/2000 | Donofrio | A61B 1/126 |
| | | | | 600/114 |
| 6,165,123 | A * | 12/2000 | Thompson | A61B 1/00078 |
| | | | | 600/114 |
| 6,520,907 | B1 | 2/2003 | Foley et al. | |
| 8,118,731 | B2 * | 2/2012 | Kucklick | A61B 17/3423 |
| | | | | 600/114 |
| 9,232,937 | B2 | 1/2016 | Alleyne | |
| 9,782,157 | B2 | 10/2017 | Novak et al. | |
| 9,808,603 | B2 * | 11/2017 | Yamazaki | A61M 3/0279 |
| 10,398,292 | B2 * | 9/2019 | Drach | A61M 5/31 |
| 2002/0022764 | A1 * | 2/2002 | Smith | A61B 17/3417 |
| | | | | 600/114 |
| 2008/0214898 | A1 * | 9/2008 | Warren | A61B 17/02 |
| | | | | 600/210 |
| 2010/0125171 | A1 | 5/2010 | Kelner | |
| 2013/0138036 | A1 | 5/2013 | Solomon et al. | |
| 2017/0156814 | A1 | 6/2017 | Thommen et al. | |

OTHER PUBLICATIONS

Acton, Q. Ashton, Advances in Surgery Research and Application 2013 Edition; Chapter 15: Minimally Invasive Surgical Procedures.
Nomura et al., Microendoscopic Decompression Surgery for Lumbar Spinal Canal Stenosis via the Paramedian Approach: Preliminary Results; Global Spine Journal; 2012; 7 pgs.
Zhang et al., Minimally Invasive Computer Navigation-Assisted Endoscopic Transforaminal Interbody Fusion with Bilateral Decompression via a Unilateral Approach: Initial Clinical Experience at One-Year Follow-Up; World Neurosurgery; Feb. 19, 2017; 27 pgs.
Abbasi et al., Computerized lateral endoscopic approach to spinal pathologies; International Congress Series 1230 (2001) 240-247; 8 pgs.
Choi et al., Endoscopic Spine Surgery; The Korean Neurological Society; Sep. 2017; 13 pgs.

* cited by examiner

INSTRUMENTATION AND SURGICAL METHOD FOR IMAGE-GUIDED MICROENDOSCOPIC DECOMPRESSION

CROSS-REFERENCE TO RELATED APPLICATIONS

This application claims benefit of U.S. Provisional Application No. 62/617,975, filed Jan. 16, 2018, entitled INSTRUMENTATION AND SURGICAL METHOD FOR IMAGE-GUIDED MICROENDOSCOPIC DECOMPRESSION.

TECHNICAL FIELD

The present disclosure relates generally to methods and instrumentation for microendoscopic surgery and, more specifically, to a method and instrumentation for performing microendoscopic decompression of the spinal anatomy.

BACKGROUND

Compression of the spinal cord and nerves, known as spinal stenosis, is a common problem that results when bone, disc, or ligamentous structures encroach on the spinal canal and cause pressure on neurologic structures. FIG. 1 demonstrates the anatomic structures that contribute to neurologic compression. This pressure results in arm or leg pain, numbness, and/or weakness. The removal of these structures that encroach on the neurologic structures, known as decompression surgery, is one of the most common procedures performed in spinal surgery. FIG. 2 depicts the bony and ligamentous structures removed during a decompression surgery. In order to gain access to these structures, surgeons traditionally make incisions and must move or dissect structures, including muscles and ligaments, in order to perform decompression surgery. This results in permanent changes to these muscles and ligaments and can result in destabilization of the spinal segments, causing functional limitations, mechanical pain, and possibly leading to further surgery.

More recently surgeons have utilized small tubular retractors, which can be placed between and through muscle fibers, allowing access to the spinal canal with less muscle and ligament disruption. Surgeons have traditionally used a microscope to view the spinal canal through the tube, but this provides limited visibility and a field of view, which is limited to the area of the tube.

The problem of limited field of view has been in part improved upon by utilizing a small camera placed into the tube, which can be moved to different positions, thus allowing improved visualization and increased field of view, outside the area of the tube, known as microendoscopic spine surgery. Microendoscopic surgery is very much akin to arthroscopic surgery of the knees and shoulders, which has gained rapidly in utilization since its inception, as it similarly allows for the manipulation of tissues deep inside the body while minimizing the detriment to the surrounding structures. As was similarly the case in arthroscopic surgery decades ago, microendoscopic spine surgery is limited at this early stage in development by the lack of tools and techniques to effectively and safely achieve decompression of the neurologic structures through a smaller working portal with less direct visualization.

One of the unique challenges to spinal anatomy, as compared to that of a shoulder or knee, is the reduced ability to differentiate regional anatomy. In traditional open spinal surgery, the surgeon can directly visualize the facet joints and pars, which define the borders of the spinal canal, and must be preserved during the decompression surgery in order to maintain the stability of the spinal segment. Visualizing these structures requires further tissue dissection, which defeats the purpose of less invasive surgery, and is less feasible when viewing them indirectly, with a camera, in the absence of clear regional identifiable anatomy.

The advent of intraoperative three dimensional or multi-planar (CT or MM) imaging and navigation techniques have provided surgeons the ability to view real time multi-planar images in the operating room, and further, the ability to track and view the location of instruments relative to anatomic structures on multi-planar views.

Navigated microendoscopic spine surgery represents the incorporation of these two technologies. While microendoscopic surgery allows for minimally invasive and minimally disruptive access to the spinal canal, and the use of a camera increases the field of view significantly over direct visualization externally with a microscope, it creates the challenge of the inability to define regional anatomy, which can be resolved by coupling navigation technology to microendoscopic instrumentation and techniques. The current systems have limitations due to retractor design and are based in a dry environment with intermittent irrigation and suction managed by the operator.

The limitations of the retractor, instruments, and technique will be resolved with this novel system.

SUMMARY

The proposed invention is a novel concept, system, and technique for multi-planar (CT or MRI) image-guided microendoscopic spinal surgery.

In one aspect, instrumentation for microendoscopic surgery comprises a retractor having a tubular wall defining an interior passage extending between a proximal end and a distal end. The tubular wall of the retractor including a fluid irrigation system having a plurality of irrigation outlet holes disposed circumferentially around the interior passage adjacent the distal end, an irrigation inlet positioned adjacent the proximal end and at least one irrigation channel fluidly connecting the irrigation inlet to the plurality of irrigation outlet holes. A camera including an imaging lens is disposed within the interior passage of the retractor proximal to the irrigation holes. The imaging lens provides a field of view extending in a distal direction past the distal end of the retractor. A removable multi-planar navigation marker is mounted to the retractor in a first predetermined multi-planar spatial relation to the distal end of the retractor.

In one embodiment, a portion of the tubular wall of the retractor excluding only the distal end is substantially radiolucent.

In another embodiment, the distal end of the tubular wall of the retractor is substantially radiopaque.

In a further embodiment, the tubular wall of the retractor further comprises a fluid suction system having a plurality of suction inlet holes disposed circumferentially around the interior passage at a position proximal to the camera imaging lens, a suction outlet disposed adjacent the proximal end and at least one suction channel fluidly connecting the suction outlet to the plurality of suction inlet holes.

In yet another embodiment, the instrumentation further comprises a dilator having a body with a distal dilator tip and multi-planar navigation marker mounted to the dilator in a second predetermined multi-planar spatial relation to the distal dilator tip.

In yet another embodiment, the instrumentation further comprises a navigated microendoscopic burr having a cutting head, the burr being configured to be inserted through the interior passage of the retractor until the cutting head is disposed distally beyond the distal end of the tubular wall. When the cutting head is disposed distally beyond the distal end of the tubular wall, the cutting head is within the field of view of the imaging lens of the camera.

In a further embodiment, the instrumentation further comprises a navigated osteotome having a cutting blade, the osteotome being configured to be inserted through the interior passage of the retractor until the blade is disposed distally beyond the distal end of the tubular wall. When the blade is disposed distally beyond the distal end of the tubular wall, the blade is within the field of view of the imaging lens of the camera.

In another aspect, a surgical method of microendoscopic decompression on a patient, comprises creating a skin opening in a patient and placing a retractor through the skin opening and into proximity to a spinolaminar juction using multiplanar imaging. The retractor includes a tubular wall defining an interior passage extending between a proximal end and a distal end. The tubular wall of the retractor includes a fluid irrigation system having a plurality of irrigation outlet holes disposed circumferentially around the interior passage adjacent the distal end, an irrigation inlet positioned adjacent the proximal end and at least one irrigation channel fluidly connecting the irrigation inlet to the plurality of irrigation outlet holes. A camera including an imaging lens is disposed within the interior passage of the retractor proximal to the irrigation holes. The imaging lens provides a field of view extending in a distal direction past the distal end of the retractor. A removable multi-planar navigation marker is mounted to the retractor in a first predetermined multi-planar spatial relation to the distal end of the retractor. Surgical instruments are inserted through the interior passage of the retractor past the distal end of the retractor and into the field of view of the camera. Positions of the surgical instruments are observed in the field of view using the camera, and can be monitored and navigated on multi-planar imaging. The surgical field can be irrigated via the irrigation system in the retractor and differentially controlled in combination with suction to create either a dry or fluid submerged surgical field.

In yet another aspect, instrumentation for microendoscopic surgery comprises a first retractor having a tubular wall including an inner surface and an outer surface, the interior surface defining an interior passage extending between a proximal end and a distal working end. A multi-planar navigation marker is mounted to the outer surface of the tubular wall, the multi-planar navigation marker including a plurality of spaced-apart, radiopaque marker bodies. The multi-planar navigation marker is disposed at predetermined multi-planar spatial and rotational relation to the distal working end of the retractor.

In one embodiment, the tubular wall of the first retractor further comprises a fluid irrigation system including at least one irrigation outlet hole formed on the inner surface of the tubular wall and disposed adjacent to the distal working end, at least one irrigation inlet hole formed on the outer surface of the tubular wall and disposed proximally relative to the at least one irrigation inlet hole, and a first fluid-tight passage connecting between the at least one irrigation inlet hole and the at least one irrigation outlet hole for transporting fluid therebetween.

In another embodiment, the first fluid-tight passage is formed within the tubular wall of the first retractor between the inner surface and the outer surface so as to be undetectable on an inner contour of the inner surface or on an outer contour of the outer surface.

In yet another embodiment, the tubular wall of the first retractor further comprises a fluid suction system including at least one suction inlet hole formed on the inner surface of the tubular wall and disposed proximally relative to the at least one irrigation outlet hole, at least one suction outlet hole formed on the outer surface of the tubular wall, and a second fluid-tight passage connecting between the at least one suction inlet hole and the at least one suction outlet hole for transporting fluid therebetween. The first fluid-tight passage is fluidly isolated from the second fluid-tight passage.

In still another embodiment, the second fluid-tight passage is formed within the tubular wall of the first retractor between the inner surface and the outer surface so as to be undetectable on an inner contour of the inner surface or on an outer contour of the outer surface.

In a further embodiment, the instrumentation further comprises a camera assembly including an elongated camera body and a lens disposed at a distal end of the camera body. The elongated camera body is configured to be insertable through the proximal end of the first retractor and positionable in the passage of the retractor such that the lens is disposed distal to the at least one suction inlet hole and proximal to the at least one irrigation outlet hole.

In a yet further embodiment, the instrumentation further comprises a second tubular retractor having a second tubular wall having an inner surface and an outer surface, the interior surface defining an interior passage extending between a proximal end and a distal working end. The tubular wall of the first retractor has a first diameter, and the second tubular wall of the second retractor has a second diameter that is smaller than the first diameter.

In a still further embodiment, the second tubular retractor further comprises a second multi-planar navigation marker mounted to the outer surface of the second tubular wall, the second multi-planar navigation marker including a plurality of spaced-apart, radiopaque marker bodies. The second multi-planar navigation marker is disposed at predetermined multi-planar spatial and rotational relation to the distal working end of the second retractor.

In another embodiment, the instrumentation further comprises a camera assembly including a lens and an outer housing sheath surrounding the distal end of the lens, thereby forming an annular space between the outer housing sheath and the camera lens. The outer housing sheath is configured to be insertable through the proximal end of at least one of the first and second tubular retractors and extend towards the distal working end of the respective retractor. The annular space is fluidly connectable to a suction source such that, when the annular space is connected to the suction source, any fluid is drawn off the lens into the annular space.

BRIEF DESCRIPTION OF THE DRAWINGS

For a more complete understanding, reference is now made to the following description taken in conjunction with the accompanying Drawings in which:

FIGS. 4a-4c show additional details of the initial dilator assembly of FIG. 3, wherein FIG. 4a is an exploded side view, FIG. 4b is a cross-sectional end view of the initial dilator taken through line 4b-4b of FIG. 4a, and FIG. 4c is a cross-sectional end view of the probe navigational marker taken through line 4c-4c of FIG. 4a;

FIGS. 6a and 6b show additional details of the retractor system of FIG. 5, wherein FIG. 6a is a side view of the final retractor and navigation marker, and FIG. 6b is an end view of the final retractor, sequential dilators and initial probe showing the nested of these elements;

FIGS. 17 and 18 are schematic views of an exemplary retractor system including a navigated burr in accordance with another aspect positioned near the lumbar spine portion of FIG. 1, wherein FIG. 17 shows the burr in a first position allowing the working end of the burr to be directed toward the operator and more effectively remove bone on the side ipsilateral to the working tubular retractor, and FIG. 18 shows the burr in a second position allowing the working end of the burr to be directed away from the operator and more effectively remove bone on the side contralateral to the working tubular retractor;

FIGS. 20 and 21 are schematic views of an exemplary retractor system including a navigated angled osteotome in accordance with yet another aspect positioned near the lumbar spine portion of FIG. 1, wherein FIG. 20 shows the osteotome in a first position allowing the angled working end of the osteotome to be directed toward the lateral recess ipsilateral to the operator, and FIG. 21 shows the osteotome repositioned so the angled working end is directed toward the lateral recess contralateral to the operator.

DETAILED DESCRIPTION

Figure 1:
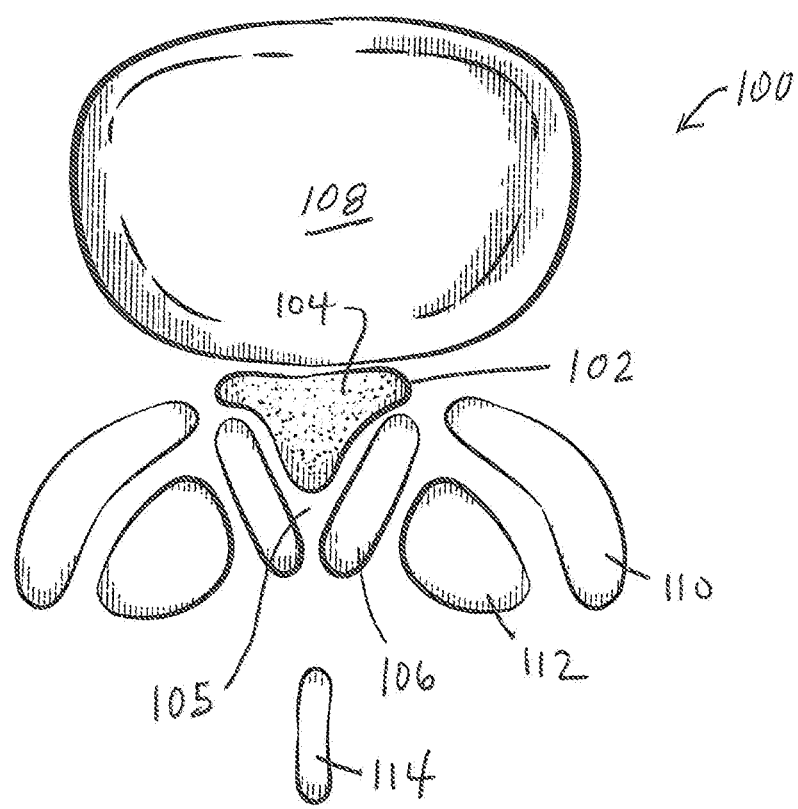
FIG. 1 is a cross-sectional representation of a portion of the lumbar spine illustrating the relevant anatomic structures associated with compression of the neural elements.

Referring now to the drawings, wherein like reference numbers are used herein to designate like elements throughout, the various views and embodiments of instrumentation and surgical method for image-guided microendoscopic decompression are illustrated and described, and other possible embodiments are described. The figures are not necessarily drawn to scale, and in some instances the drawings have been exaggerated and/or simplified in places for illustrative purposes only. One of ordinary skill in the art will appreciate the many possible applications and variations based on the following examples of possible embodiments.

Figure 2:
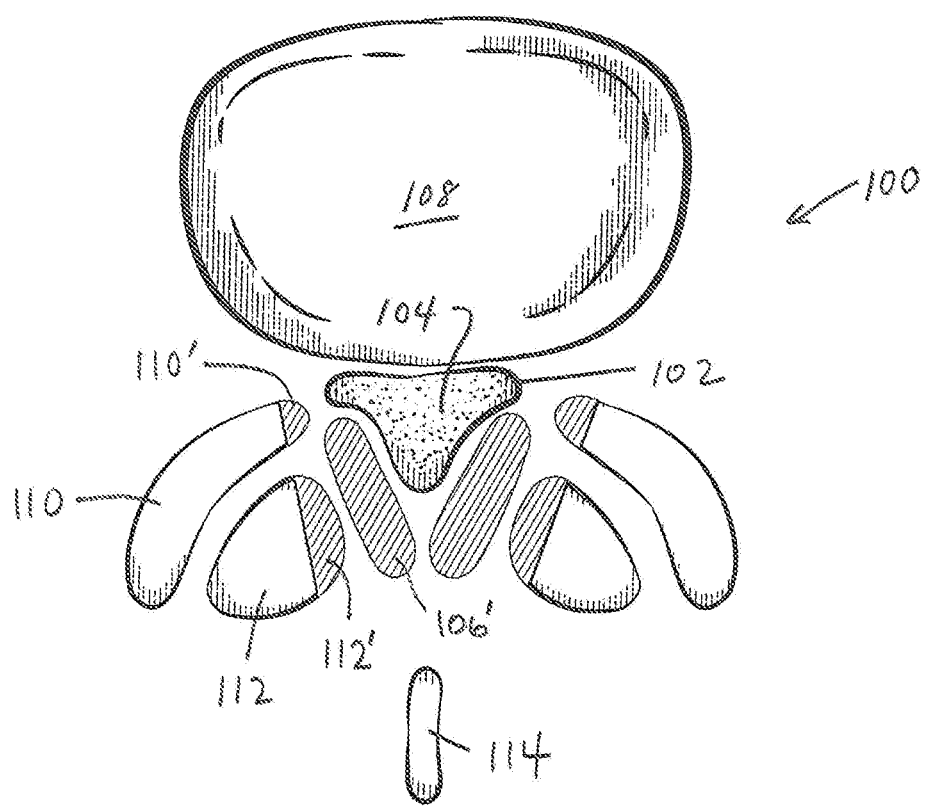
FIG. 2 is a cross-sectional view of the lumbar spine portion from FIG. 1 illustrating an exemplary decompression plan designating areas of bone and ligament that need to be removed in order to decompress the neural elements.

Referring now to FIGS. 1 and 2, an exemplary cross-section of a lumbar spine region 100 is shown to illustrate the anatomic structures associated with spinal stenosis. A dural sac 102 holding neural elements 104 of the spinal cord and nerves is disposed in a spinal canal 105 formed between a ligamentum flavum 106 and a disc 108. The ligamentum flavum 106 is flanked by superior articular process 110, interior articular process 112 and spinous process 114. Neurological compression occurs when any of these bone, disc, or liagamentous structures encroach on the spine canal 105 and put pressure on the dural sac 102 and neural elements 104 therewithin. In many cases, a bulging or rupturing of the disc 108 presses the dural sac 102 against the ligamentum flavum 106, which is rigidly supported by the adjacent articular processes 110 and 112. Decompression surgery involves the removal of selected anatomical structures to locally enlarge the spinal canal 105 and relieve the pressure on the dural sac 102 and neural elements 104.

FIG. 2 represents one example of a surgical decompression plan for the lumbar spine region 100 of FIG. 1. Portions of the anatomical structure (denoted with section lines in FIG. 2) can be removed to increase the area of the spinal canal 105 and relieve pressure on the dural sac 102 and neural elements 104. The structures to be removed during decompression can be referred to as "target structures." In the example shown, the target structures to be removed include the entire ligamentum flavum 106' and proximal ends 110' and 112' of the respective superior articular process 110 and interior articular process 112. It will be understood that the removal of the target structures typically occurs along a vertically localized section of the spine to increase the size of the spinal canal 105 vertically proximal to the stenosis. It will also be understood that the anatomical structures and surgical plan shown in FIGS. 1 and 2 are exemplary only, and use of the methods and apparatus disclosed herein is not limited thereto, but can be applied to other anatomical structures and surgical plans.

1) Localization and Retractor Placement

To perform a decompression surgery such as that depicted in the plan of FIG. 2, the surgeon must gain access the target structures, for example ligamentum flavum 106' and the target portions 110' and 112' of the respective articular processes. Appropriate placement and positioning of the tubular retractor system is imperative for optimizing access to the spinal canal 105 and thus allowing the operator to effectively perform decompression surgery. Both the position and vector of the tubular system are vital. Plain radiography is traditionally utilized for positioning of the tubular retractor, which has limited ability to define these spatial relationships.

Referring now to FIGS. 3, 4a-c, 5 and 6a-b, there is illustrated a novel retractor system 300 including an initial dilator assembly and series of successively larger nested dilators. The retractor system 300 is used to accurately position a final retractor 500, through which the surgical instruments can be inserted to perform the decompression. Markers are attached to the initial dilator and final retractor to allow three-dimensional positional tracking via radio imaging (e.g., radiography or fluoroscopy). Navigation is important for positioning the initial dilator and to confirm the position of the final retractor.

Figure 3:
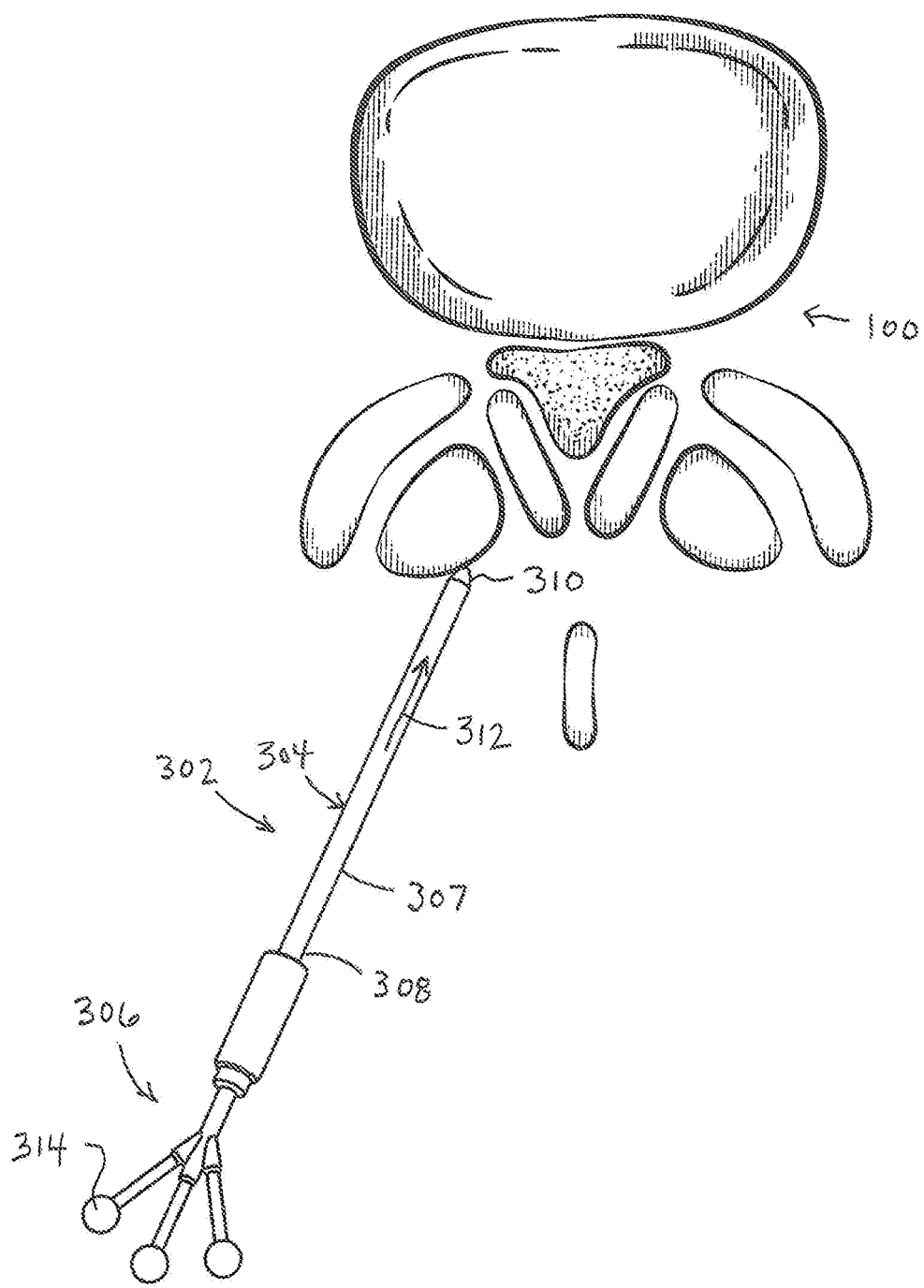
FIG. 3 is a schematic view of an exemplary initial dilator assembly in accordance with one aspect positioned adjacent to the lumbar spine portion of FIG. 1, the initial dilator assembly including a probe dilator and a detachable marker holder for multi-planar image guidance.

Referring first to FIG. 3, an initial dilator assembly 302 is illustrated in the context of the anatomical structures of the lumbar spine region 100. The initial dilator assembly 302 includes an initial dilator 304, also called a probe, connected to a probe navigation marker 306. The probe 304 has an elongated body 307 extending between a proximal end 308 and a distal tip 310. The body 307 of the probe 304 typically has a cylindrical cross section of a first diameter and defines a probe vector 312 extending therebetween directed towards the distal tip 310. The probe navigation marker 306 is connected to the proximal end 308 of the probe 304 and includes multiple marker bodies 314 disposed at predetermined positions relative to the distal tip 310. The marker bodies 314 are typically formed of materials visible via radio imaging, thus, the marker bodies allow both the location of the distal tip 310 and orientation of the probe vector 312 to be determined and/or tracked via radio imaging.

As the procedure begins, the probe 304 is inserted thorough an incision until the distal tip 310 is adjacent to the target structure and the vector 312 of the probe is oriented as desired by the operator. At this point, the position and orientation of the marker bodies 314 on the probe navigation marker 306 can be imaged to provide a record for later positioning of the final retractor 500. A plurality of nested dilators 316, for example, n nested dilators 316(1), 316(2) . . . 316(n), are subsequently inserted through the incision over the initial probe 304 in telescoping fashion, each successive nested dilator having a successively larger diameter than the previous nested dilator. To facilitate placement of the successive nested dilators 316 over the probe 304 without removal from the incision, the probe navigation marker 306 can be removably connected to the proximal end 308 of the probe, for example by a detachable collar 318. Thus, after positioning the probe 304 and imaging the marker bodies 314 of the navigation marker 306, the probe navigation marker including the collar 318 is removed, allowing for the successive nested dilators 316(1) . . . 316(n) to be placed over the probe and into the incision.

Figure 4A:
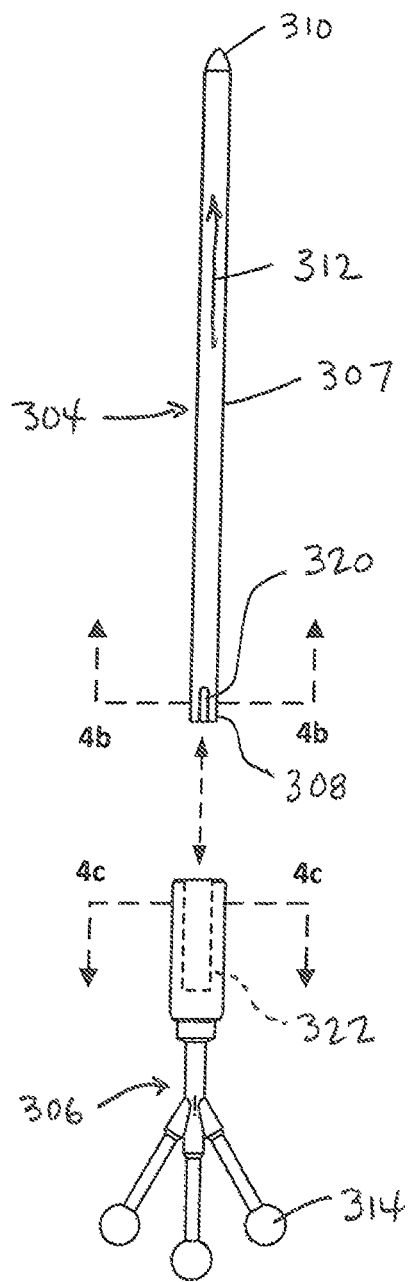
Figure 4B:
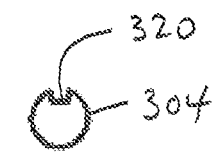
Figure 4C:
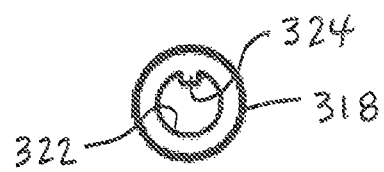

Referring now also to FIGS. 4a-c, the probe 304 and the probe navigation marker 306 can be respectively configured such that the probe connects to the probe navigation marker in a reproducible and predictable position, i.e., such that the marker bodies 314 of the probe navigation marker are disposed at a known and constant position, including both spatial and angular positions, relative to the probe tip 310. In the embodiment illustrated in FIG. 4a-c, the proximal end 308 of the probe 304 is configured with a slot 320, and the collar 318 of the navigation marker 306 is configured with a matching socket 322 having a key 324. The socket 322 can be dimensioned to accept the proximal end 308 of the probe 304 to a predetermined depth, but only when the marker 306 is rotated to orient the key 324 to a predetermined orientation such that the key fits within the slot 320. In this manner, the probe 304 connects to the probe navigation marker 306 in a totally reproducible and predictable position in terms of both spatial position and angular position. The complimentary slot 320 and key 324 of the embodiment illustrated in FIGS. 4a, 4b and 4c is only one example of configuring the probe 304 and the probe navigation marker 306 for predictable spatial and angular interconnection, and should not be considered limiting. In other embodiments, the probe 304 and the probe navigation marker 306 can be configured, respectively, with any set of complementary structures suitable for interconnection in only a single predetermined spatial and angular orientation relative to one another.

Figure 5:
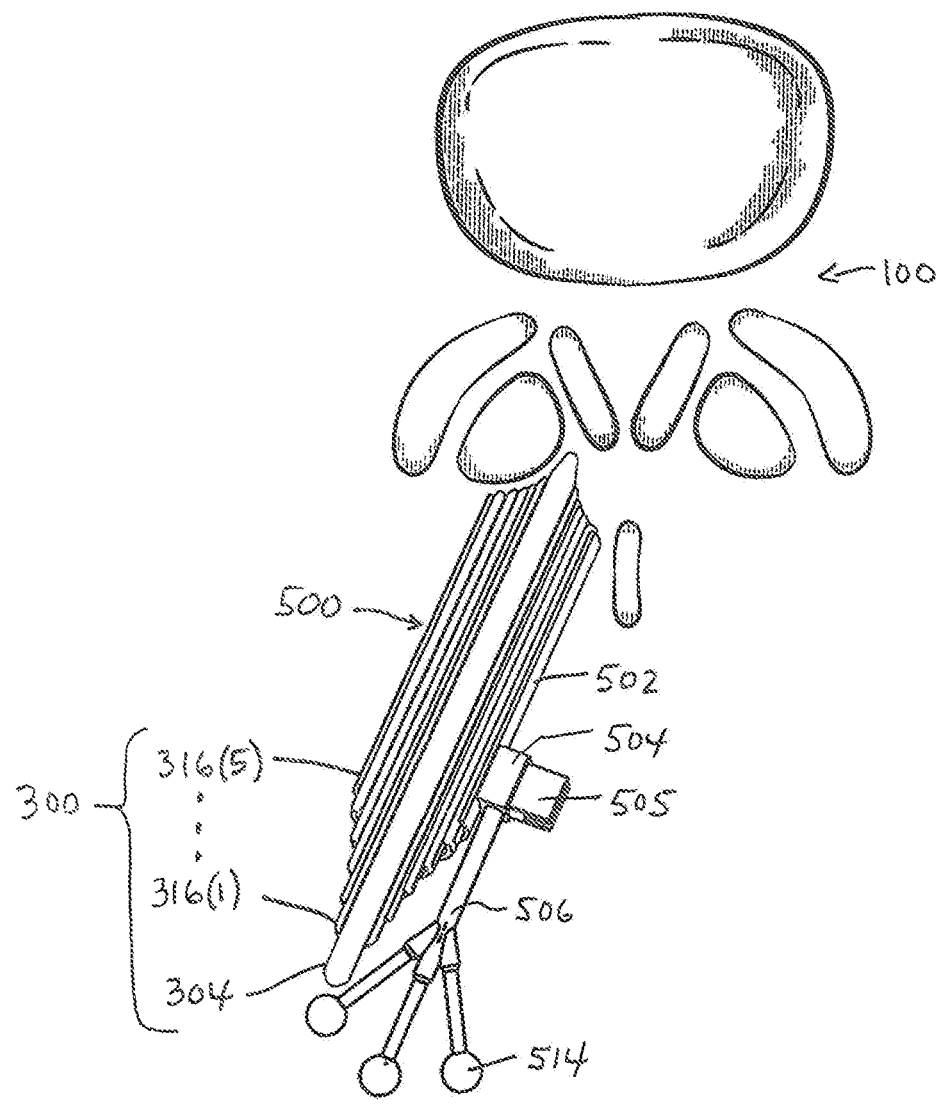
FIG. 5 is a partial cross sectional view of an exemplary retractor system in accordance with another aspect positioned adjacent to the lumbar spine portion of FIG. 1, the retractor system including sequential dilators placed over the initial probe of FIG. 3 and a final retractor with detachable marker holder for multi-planar image guidance, wherein the final retractor includes an attached housing for the navigation marker, which has a keyhole configuration for directional fit of the navigation marker.

Referring now to FIG. 5, there are illustrated the retractor system 300 and the final retractor 500 positioned proximate to the target structures in the lumbar spine region 100. For purposes of illustration, portions of the plurality of nested dilators 316 and the final retractor 500 are shown broken away in FIG. 5 to more clearly show the nested configuration. In FIG. 5, the probe navigation marker 306 has already been removed from the proximal end 308 of the probe 304, and five successively nested dilators 316, namely 316(1), 316(2), 316(3), 316(4), and 316(5), have been placed over the probe in telescoping fashion. In other embodiments, a different number of successively nested dilators can be used.

Figure 6B:
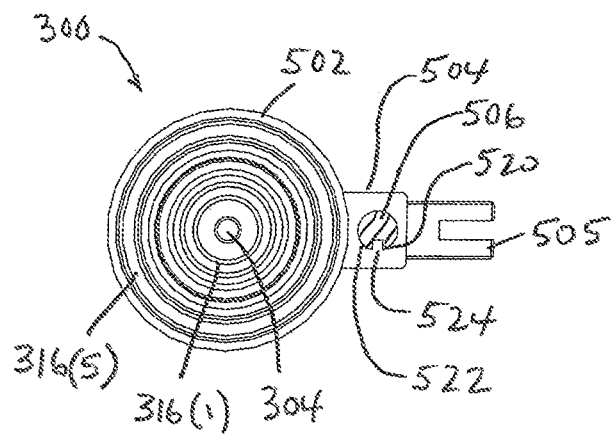
Figure 6A:
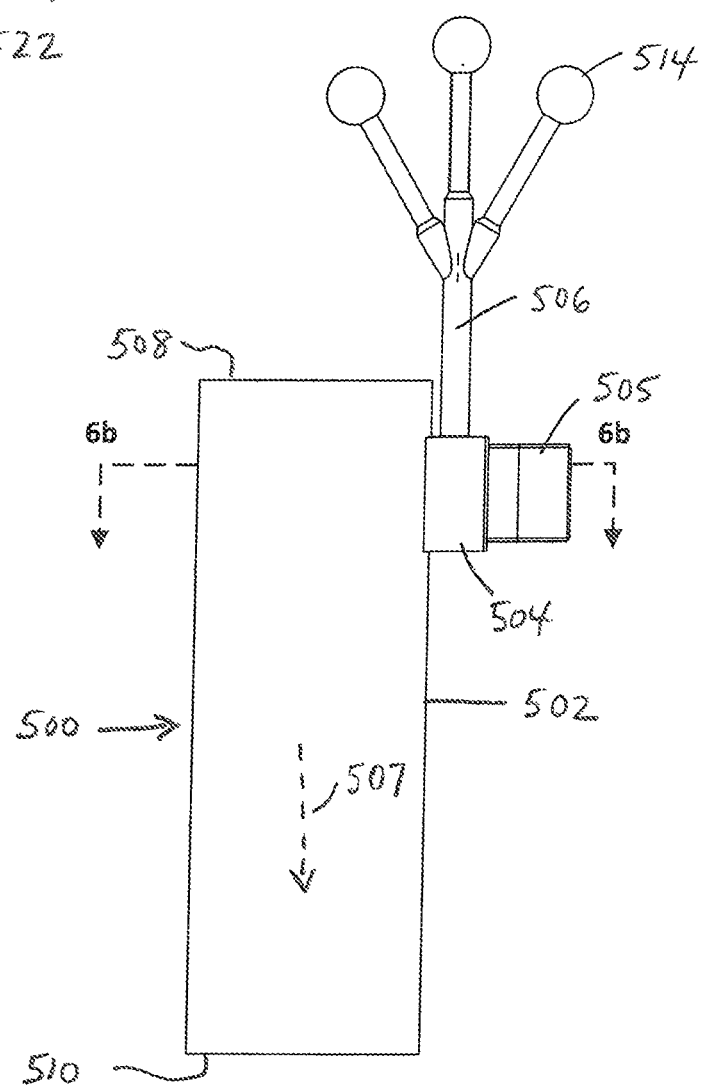

Referring now also to FIGS. 6a and 6b, the final retractor 500 includes a tubular body 502 defining an interior passage 507 extending between a proximal end 508 and a distal end 510. A marker mount 504 is attached to the tubular body 502 at a predetermined spatial and angular position from the distal end 510. A table arm mount 505 is also attached to the tubular body 502. In the illustrated embodiment, the table arm mount 505 is attached to the marker mount 504, but this is not required. Once the tubular body 502 of the final retractor 500 is placed over the largest nested dilator (i.e., dilator 316(5) in the illustrated embodiment), a retractor navigation marker 506 can be attached to the marker mount 504. The retractor navigation marker 506 includes multiple marker bodies 514 disposed at predetermined positions relative to the marker mount 504, and thus also relative to the distal end 510 of the final retractor 500. The marker bodies 514 are typically formed of materials visible via radio imaging, thus the marker bodies allow both the location of the distal tip 510 and angular orientation of the passage 507 to determined and/or tracked via radio imaging.

The retractor navigation marker 506 allows for placement and angulation of the final retractor 500 before fixing the arm connector 505 to a table-mounted arm 702 (FIG. 7), after which the spatial and angular position of the final retractor will be maintained during subsequent procedures. The imaged spatial and angular position of the retractor navigation marker 506 can also be compared to the previously recorded spatial and angular position of the probe navigation marker 306 to thereby determine placement/orientation of the distal end 510 of the final retractor 500 compared to the original placement/orientation of the distal end 310 of the probe 304. In the illustrated embodiment, the retractor navigation marker 506 is similar, but not identical to the probe navigation maker 306. In other embodiments, the same navigation marker can be used for the retractor navigation marker 506 and the probe navigation maker 306. As long as the spatial and angular positions of the respective navigation markers 306 and 506 are known relative to the respective distal probe tip/distal retractor end 310 and 510, the positions of the distal probe tip relative to the distal retractor end can be determined from imaging, e.g., radio imaging, of the respective navigation markers.

Referring now specifically to FIGS. 6a and 6b, there are provided additional views of the retractor system 300 and the final retractor 500. FIG. 6a is a side view of the final retractor 500, showing the tubular body 502, marker mount 504, table arm connector 505, and retractor navigation marker 506. FIG. 6b is a cross-sectional end view showing final retractor 500 and portions of the retractor system 300 including the probe 304 and nested dilators 316(1) . . . 316(5). It will be appreciated that the only portion of the retractor navigation marker 506 visible in the cross section of FIG. 6b is the portion within the socket 522.

The marker mount 504 and the retractor navigation marker 506 can be respectively configured such that the marker mount connects to the retractor navigation marker in a reproducible and predictable position, i.e., such that the marker bodies 514 of the retractor navigation marker are disposed at a known and constant position, including both spatial and angular positions, relative to the distal end 510 of the tubular body 502. In the embodiment illustrated in FIGS. 6a and 6b, the retractor navigation marker 506 is configured with a slot 520 and the marker mount 504 is configured with a matching socket 522 having a key 524. The socket 522 can be dimensioned to accept an end of the retraction navigation marker 506 to a predetermined depth, but only when the retraction navigation marker is rotated to orient the slot 520 to a predetermined orientation such that the key 524 fits within the slot. In this manner, the marker mount 505 connects to the retractor navigation marker 506 in a totally reproducible and predictable position in terms of both spatial position and angular position. The complimentary slot 520 and key 524 of the embodiment illustrated in FIGS. 6a and 6b is only one example of configuring the marker mount 505 and the retractor navigation marker 506 for predictable spatial and angular interconnection, and should not be considered limiting. In other embodiments, the marker mount 505 and the retractor navigation marker 506 can be configured, respectively, with any set of complementary structures suitable for interconnection in only a single predetermined spatial and angular orientation relative to one another.

Figure 7:
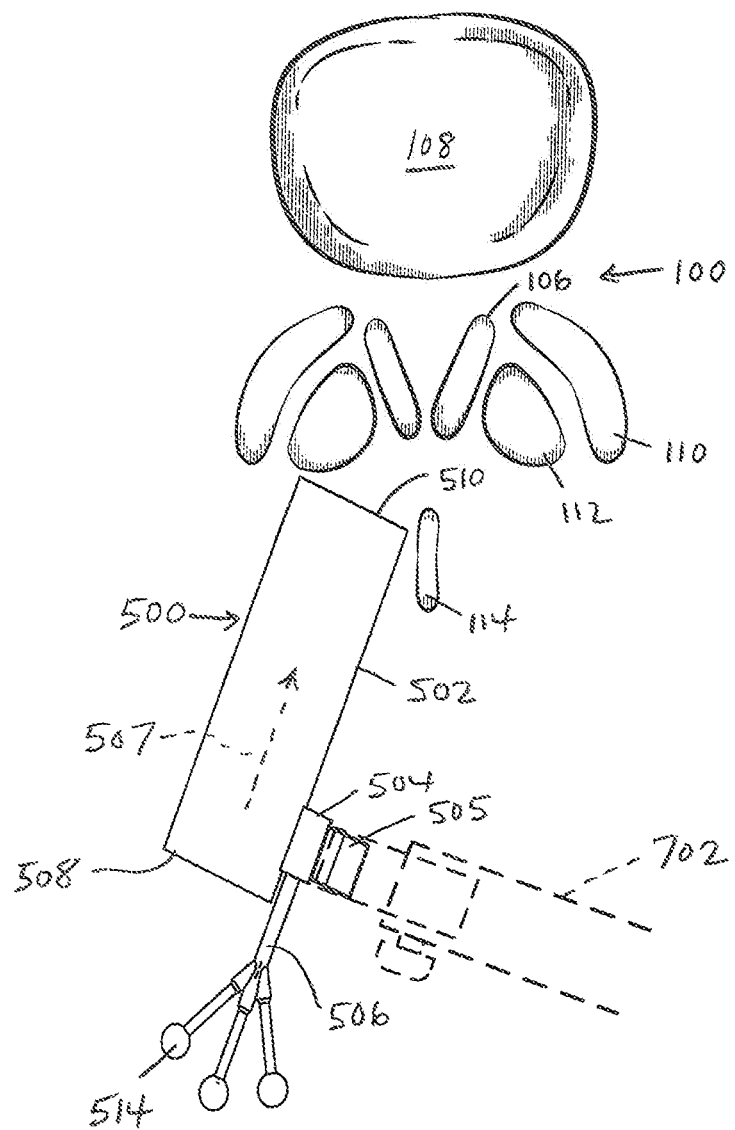
FIG. 7 is a schematic view of an exemplary retractor in accordance with another aspect positioned adjacent to the lumbar spinal portion of FIG. 1 showing the retractor attached to a table-mounted arm.

Referring now to FIG. 7, the final retractor 500 is illustrated in position adjacent to the target structures in the lumbar spinal region 100. For purposes of clarity, the dural sac 102 is not illustrated in FIG. 7. The probe 304 and the plurality of dilators 316 comprising the retractor system 300 have been removed from the passage 507 of the final retractor 500 to provide a clear access path to the target structures via the retractor passage. After imaging the retractor navigation marker 506 to verify the spatial position of the distal end 510 and the angular orientation of tubular body 502 (and hence the interior passage 507) according to the surgical plan, the final retractor 500 can be rigidly locked in position, e.g., by connection of the table arm mount 505 to a table arm 702.

Figure 8:
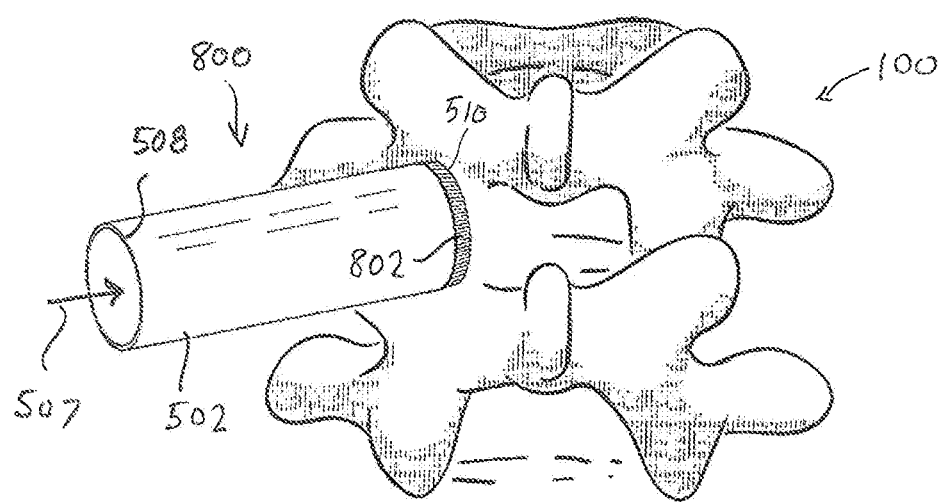
FIG. 8 is an anteroposterior (AP) perspective view of a tubular retractor with radiopaque distal retractor tip in accordance with yet another aspect positioned over a vertebral interspace.

Referring now to FIG. 8, there is illustrated another exemplary embodiment of a final retractor docked against the anatomical structures of the lumbar spinal region 100. The final retractor 800 is similar in most respects to the final retractor 500 previously described, thus identical reference numbers are used for identical features. The final retractor 800 of this embodiment includes the retractor navigation marker 506 and attachment structures 504 and 505; however, these are not shown in FIG. 8 for purposes of clarity. During spinal decompression procedures, the positioning and localization of the final retractor are of utmost importance. While a navigated system can be used to provide multi-planar localization, some surgeons may rely on intraoperative fluoroscopy, either because of individual preference, real-time feedback, or the lack of resources for navigation. For this reason, the final retractor 800 is adapted for positioning under intraoperative fluoroscopy. The surgeon can utilize anteroposterior (AP) and lateral fluoroscopic views in order to position the final retractor 800. The position of the distal end 510 of the tubular body 502 docked against the spine is the central point of interest. Surgeons may also be interested in visualizing metallic (e.g., steel) instruments placed through the passage 507 of the tubular body 502 during certain steps of the procedure. In preferred embodiments, the final retractor 800 is radiolucent through the majority of the tubular body 502 from the proximal end 508 (which is positioned outside the body), but have a radiopaque marker 802 outlining the working perimeter at the distal end 510 of the tubular passage 507 positioned next to the spine. FIG. 8 depicts the AP radiographic view of the final retractor 800 with radiopaque distal retractor tip 802 positioned over the vertebral interspace. This would allow the operator to see exactly where the borders of the distal working end 510 of the retractor 800 are positioned on plain radiography.

Figure 9:
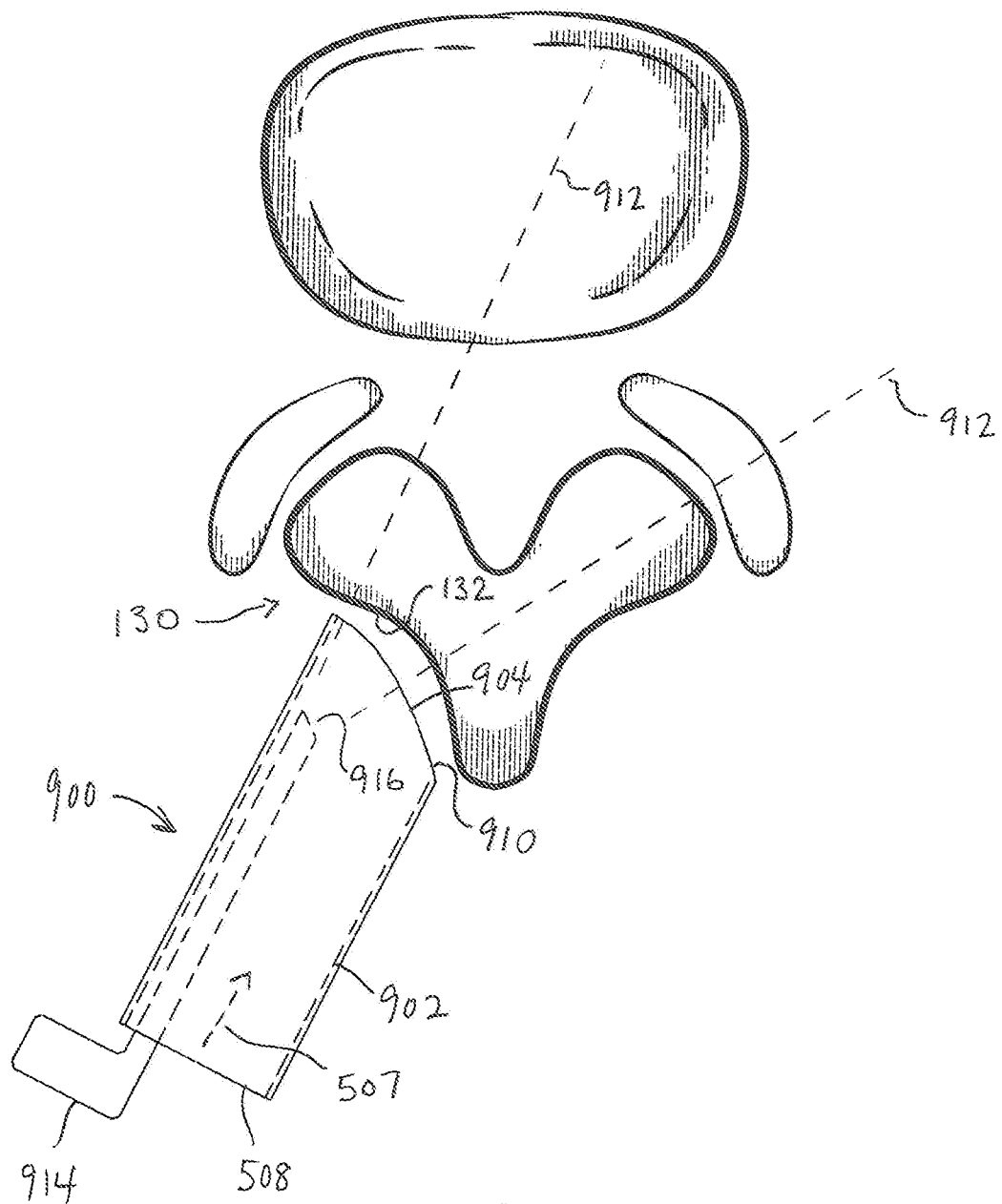
FIG. 9 is a schematic view of an exemplary retractor with beveled distal end in accordance with still another aspect positioned adjacent to a spinolaminar junction, wherein the bevel shortens the medial side of the retractor and allows for the distal retractor end to be placed nearer the midline.

Referring now to FIG. 9, there is illustrated yet another exemplary embodiment of a final retractor positioned near the anatomical structures of a spinolaminar junction 130. The final retractor 900 is similar in most respects to the final retractor 500 previously described, thus identical reference numbers are used for identical features. The final retractor 900 of this embodiment includes the retractor navigation marker 506 and attachment structures 504 and 505; however, these are not shown in FIG. 9 for purposes of clarity. Whereas the tubular body 502 of final retractor 500 has a distal end 510 that is oriented substantially perpendicular to the longitudinal passage 507, the tubular body 902 of the final retractor 900 is configured to form a bevel 904 at the distal end 910 in order to facilitate the docking of the distal end of the retractor on the curved structures 132 of the spinolaminar junction 130, as illustrated in FIG. 9. When the surgical procedure involves a bilateral decompression through a unilateral paraspinal approach, the positioning of the final retractor 900 nearest to the spinolaminar junction 130 facilitates the decompression of the contralateral spinal canal. One limitation of the previously described full (i.e., perpendicular distal end) tubular retractor 500 is that the spinolaminar junction 130 needs to be undercut in order for the tube body to be repositioned near the midline. The bevel 904 on the retractor 900 shortens the medial side of the retractor, and thus allows for the distal retractor end 910 to be placed near the midline and also allows for improved unimpaired visualization (denoted by dashed lines 912 in FIG. 9) of the contralateral spinal canal, e.g., by a camera 914 disposed in passage 507 of the retractor.

2) Microendoscopic Tube System with Irrigation and Suction

Once the tubular final retractor, e.g., retractor 500, 800 or 900 is placed and appropriately positioned, the operator can begin with the decompression. The first step is to perform the laminotomy, in which a portion of the bony elements 110, 112 and/or 114 are removed to allow access to the ligamentum flavum 106. The ligamentum flavum 106, and its midline raphe, serve as a relatively consistent anatomic landmark to demonstrate the midline. Exposure of these structures and bony removal is facilitated in some portion by a burr. The burr typically generates bony debris, which requires continual irrigation and suction in order to remove debris and allow continued visualization. Irrigation is traditionally performed by the operator using a syringe, and suction is similarly performed by manual control of a suction tip.

Figure 10:
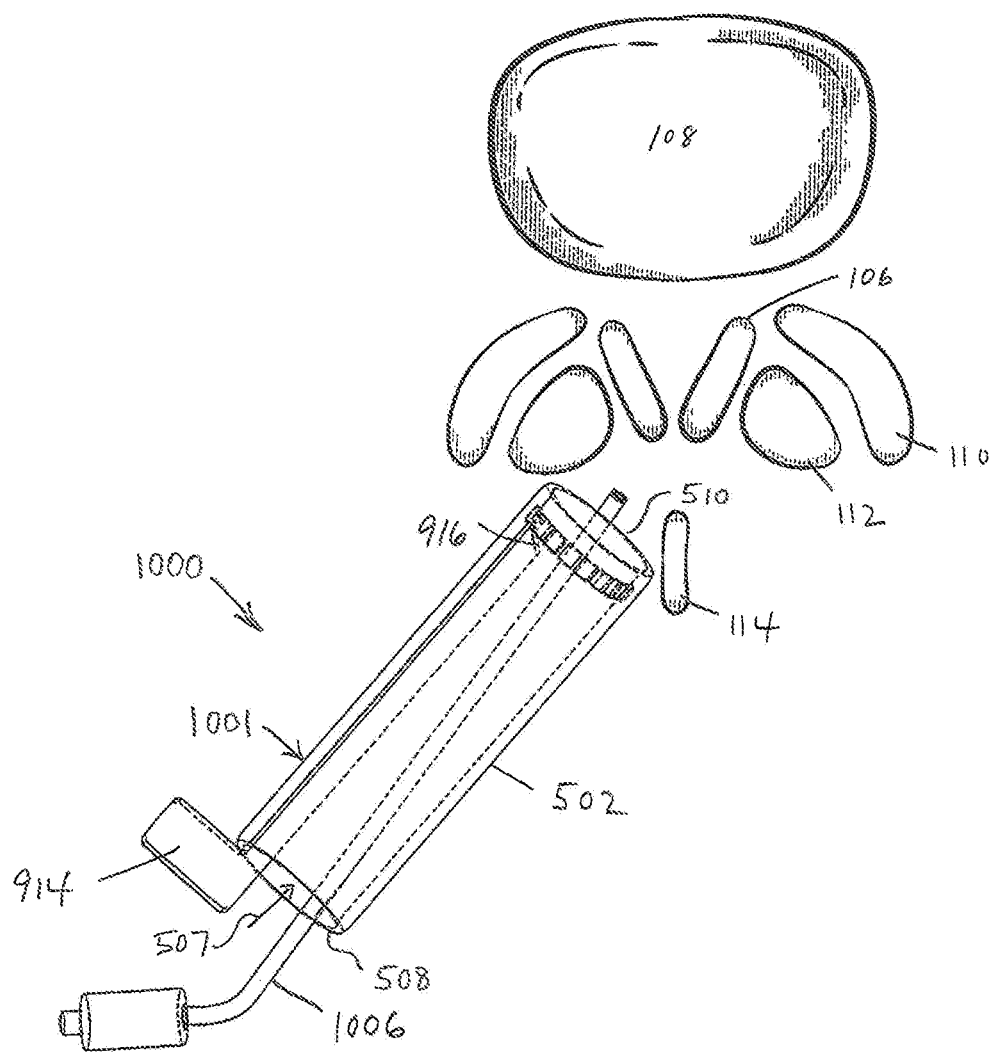
FIG. 10 is a schematic view of an exemplary tubular retractor system with irrigation system and camera in accordance with another aspect positioned near the lumbar spine portion of FIG. 1, wherein the irrigation holes are disposed distal to the camera lens so as not to have fluid obscure the view from the camera.
Figure 11:
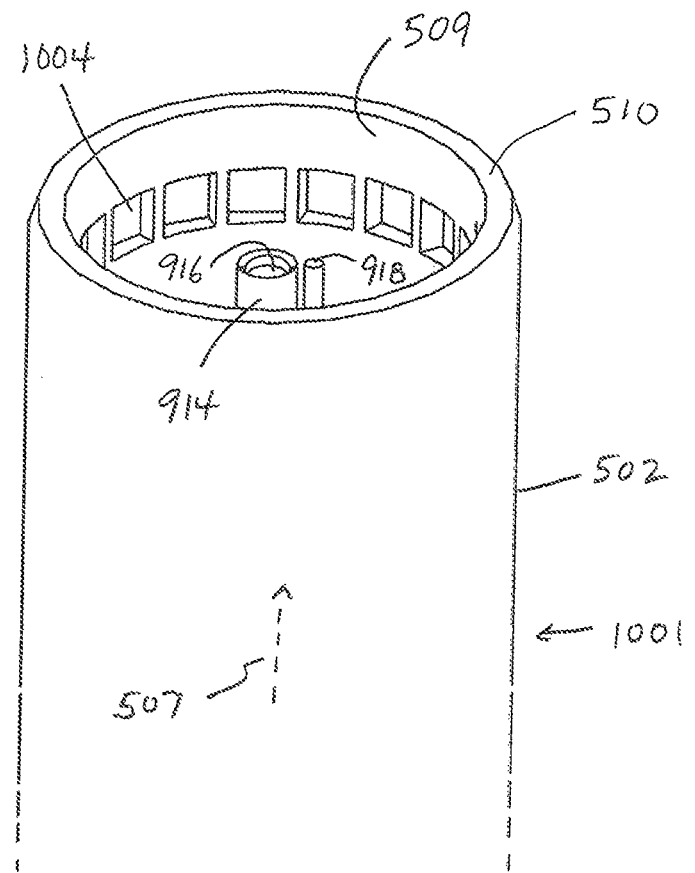
FIG. 11 is a partial perspective view of the distal working end of the tubular retractor of FIG. 10 showing the irrigation outlet holes positioned circumferentially around the inner wall and distally beyond the camera and light source so that fluid does not obscure the camera lens.

Referring now to FIGS. 10 and 11, there is illustrated another exemplary retractor system in accordance with another aspect of the disclosure. In particular, a retractor system 1000 is illustrated having irrigation features incorporated into the final retractor 1001 in order to free the operator's hands for instrumentation. Although not illustrated in FIGS. 10 and 11, the retractor system 1000 can include the previously described retractor system 300 and retractor navigation marker 506 (both shown in, e.g., FIG. 5) for insertion, placement, orientation and imaging of the final retractor 1001. In addition, the final retractor 1001 is similar in many respects to the final retractors 500, 800 and 900 previously described, thus identical reference numbers are used for identical features.

In the retractor system 1000, the tubular final retractor 1001 includes an internal irrigation system 1002 to guide a flow of an irrigation fluid (e.g., water, saline, etc.) through a fluid distribution structure of the retractor to one or more outlet holes 1004 located near the retractor's distal working end 510. In some embodiments, the fluid distribution structure of the retractor 1001 includes one or more fluid channels formed within the tubular wall 502 (i.e., between the inner and outer wall surfaces) such that the presence of the channels does not change the overall wall thickness compared to portions of the wall without the channels. In other embodiments, the fluid distribution structure of the retractor 1001 includes one or more discrete tubes or fluid channels routed along the exterior of the tubular wall 502. In still other embodiments, the fluid distribution structure of the retractor 1001 includes one or more discrete tubes or fluid channels routed along the interior wall 509 of the retractor, in which case the successively nested retractors 316 can be configured to allow clearance for such tubes/channels.

FIG. 10 shows the relative position of the camera 914, irrigation holes 1004, and a handheld suction device 1006 using phantom lines to show the elements within the passage 507. The manual controlled suction tip 1006 may be required in the working field if the retractor 1001 itself does not incorporate a suction system, or if the suction incorporated into the retractor is not able to collect fluid in the working field. In the illustrated embodiment, a plurality of circumferentially placed outlet holes 1004 are disposed along the internal wall 509 of the retractor 1001 near the distal end 510 to facilitate irrigation over the entire field of view through the internal passage 507. In the illustrated embodiment, the irrigation holes 1004 are disposed distal to the final position of the camera lens 916 such that fluid will not contact the camera lens and obscure the view during normal use. FIG. 11 provides an enlarged view of the distal end 510 of the final retractor 1001 to illustrate the relative position of the camera 914, light source 918, and irrigation outlet holes 1004. In some embodiments, water flow to the outlet holes 1004 can be controlled by a foot pedal in order to free the operator's hands for instruments and suction.

Figure 12:
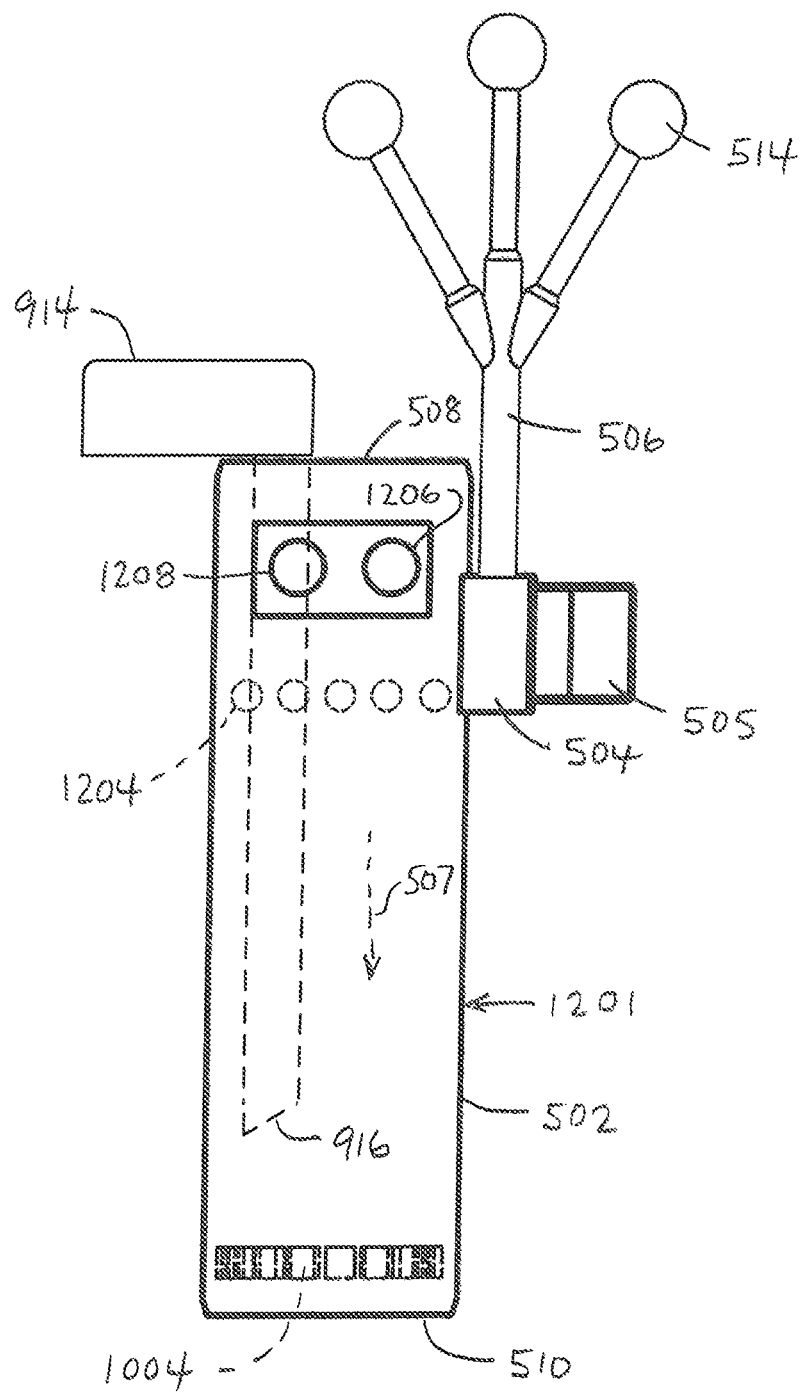
FIG. 12 is a side view of an exemplary tubular retractor system with irrigation system, suction system, camera and navigation marker in accordance with yet another aspect.
Figure 13:
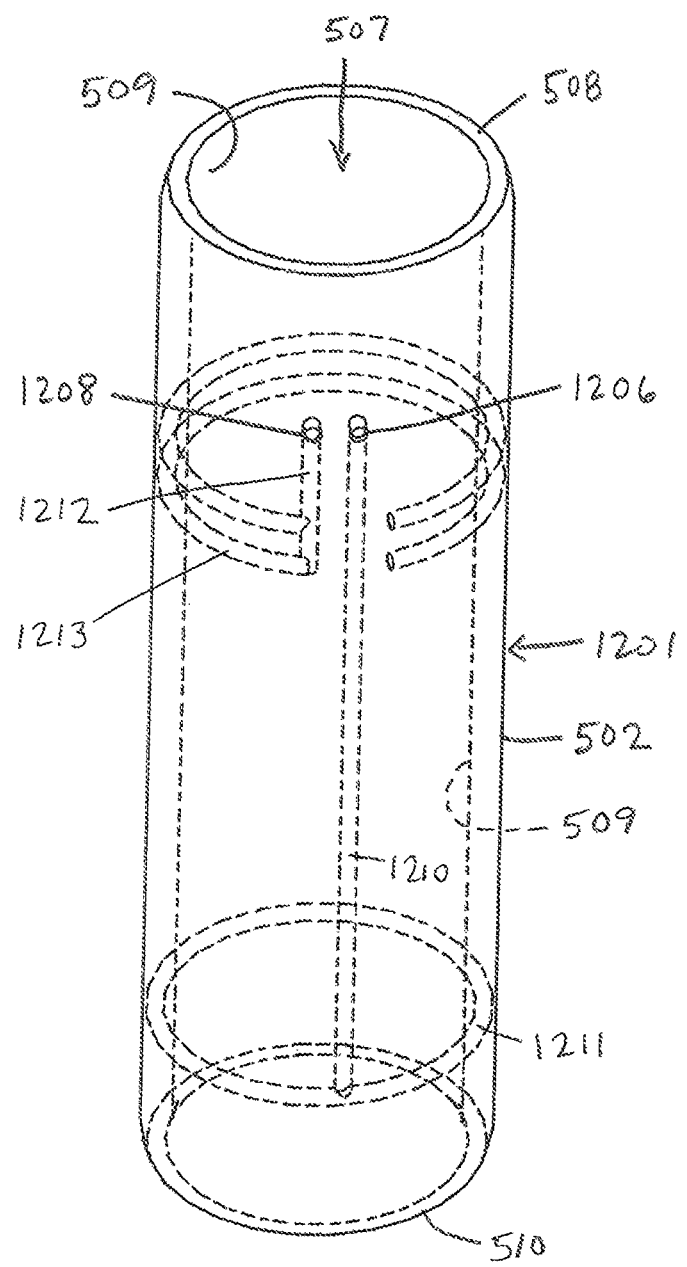
FIG. 13 is a schematic perspective view of the retractor of FIG. 12 showing the internal channels for suction and irrigation within the wall of the tubular retractor.

Referring now to FIGS. 12 and 13, there is illustrated another exemplary retractor system in accordance with another aspect of the disclosure. In particular, a retractor system 1200 includes fluid suction features in addition to fluid irrigation features incorporated into the final retractor 1201 in order to further free the operator's hands for instrumentation. Although not illustrated in FIGS. 12 and 13, the retractor system 1200 can comprise the previously described retractor system 300 for insertion, placement, orientation and/or imaging of the final retractor 1201. The final retractor 1201 is similar in many respects to the final retractors 500, 800, 900 and 1001 previously described, thus identical reference numbers are used for identical features.

The final retractor 1201 includes fluid suction features in the tubular retractor body 502. Due to the fact that the working area is beyond the distal end 510 of the tubular retractor 1201, fluid in the surgical bed must typically be removed with a separate hand-held suction device (e.g., suction wand 1006 of FIG. 10). The ability to submerge the working area of the surgical field entirely under water can provide a benefit in many situations. For instance, bone debris created when using the burr would be immediately swept away from the working field, improving visualization. Further, fluid would travel between tissue planes, such as between the ligamentum flavum and dura, making dissection and removal of tissue safer and less likely to result in dural injury.

The final retractor 1201 includes one or more suction (i.e., fluid inlet) holes 1204 and one or more irrigation (i.e., fluid outlet) holes 1004 disposed on the interior wall 509 of the tubular retractor body 502. In some embodiments, the suction holes 1204 can be disposed proximal to the irrigation holes 1004 along the internal passage 507 of the tubular body 502. In other embodiments, the suction holes 1204 can be disposed proximal to the final position (i.e., furthermost insertion point) of the camera lens 916 and the irrigation holes 1004 can be disposed distal to the final position of the camera lens. In the illustrated exemplary embodiment of FIG. 12, a first plurality of suction holes 1204 are disposed circumferentially around the interior wall 509 of the tubular body 502 at a first position along the passage 507 proximal to the final position of the camera lens 916, and a second plurality of irrigation holes 1004 are disposed circumferentially around the interior wall at a second position distal to the final position of the camera lens. The combination of the irrigation and fluid source 1004 placed distal to the camera lens 916 and the suction holes 1204 placed proximal to the camera lens will allow the system to create a working field and visualization point that are entirely submerged in fluid.

FIG. 12 illustrates the relative location of the irrigation holes 1004 and suction holes 1204 on the internal (i.e., interior) surface 509 of the retractor 1201 (the holes 1004 and 1204 are shown in broken line because they open only on the interior wall of the retractor). An irrigation fluid inlet connection 1206 and a suction outlet connection 1208 can be provided on the exterior surface of the retractor 1201. The irrigation inlet connection 1206 is in fluid connection with the irrigation outlet holes 1004, and the suction outlet connection 1208 is in fluid connection with the suction inlet holes 1204. The suction and irrigation systems are fluidly isolated from one another. The inlet connection 1206 and the outlet connection 1208 can be disposed on the proximal portion of the retractor 1201 so the connections can remain outside the patient for attachment to external suction and irrigation sources (not shown). When the irrigation fluid inlet hole 1206 is connected to a source of the irrigation fluid, the irrigation fluid can flow out from the irrigation outlet holes 1004 and into the adjacent surgical field and/or fill the tubular passage 507 of the retractor 1201. When the suction outlet connection hole 1208 is connected to a source of suction (e.g., vacuum), irrigation fluid at or near the suction inlet holes 1204 can flow into the suction inlet holes and thereby be removed from the tubular passage 507 of the retractor 1201 and/or adjacent surgical field.

Referring now specifically to FIG. 13, there is illustrated an exemplary configuration for the internal suction and irrigation channels (or manifolds) housed within the tubular retractor body 502 of the retractor 1201. The irrigation channels 1210, 1211 connect the irrigation inlet connection 1206 on the outside surface of the tubular body 502 to the irrigation outlet holes 1004 (not shown) on the inside surface 509 of the body, and the suction channels 1212, 1213 connect the suction outlet connection 1208 on the outside surface of the body to the suction inlet holes 1204 (not shown) on the inside surface of the body. In some embodiments, the irrigation channels 1210, 1211 and/or the suction channels 1212, 1213 can be disposed within the wall structure of the tubular body 502 (i.e., between the inner and outer wall surfaces) so that there is no protrusion of the channels into the interior passage 507 or other change of overall wall thickness due to the channels; however, in other embodiments, one or more of the channels may be disposed on the inner or uter surface of the tubular body. In the exemplary embodiment of FIG. 13, the channels for suction 1212, 1213 and for irrigation 1210, 1211 are configured so that there is not overlapping or crossing of the respective channels, such that thickness of the tubular retractor needed to house the respective manifolds can be minimized. As previously described, the inlet connection 1206 and outlet connection 1208 can be disposed on a proximal portion of the retractor 1201 so they can remain outside the patient for attachment to external suction and irrigation sources.

Figure 14:
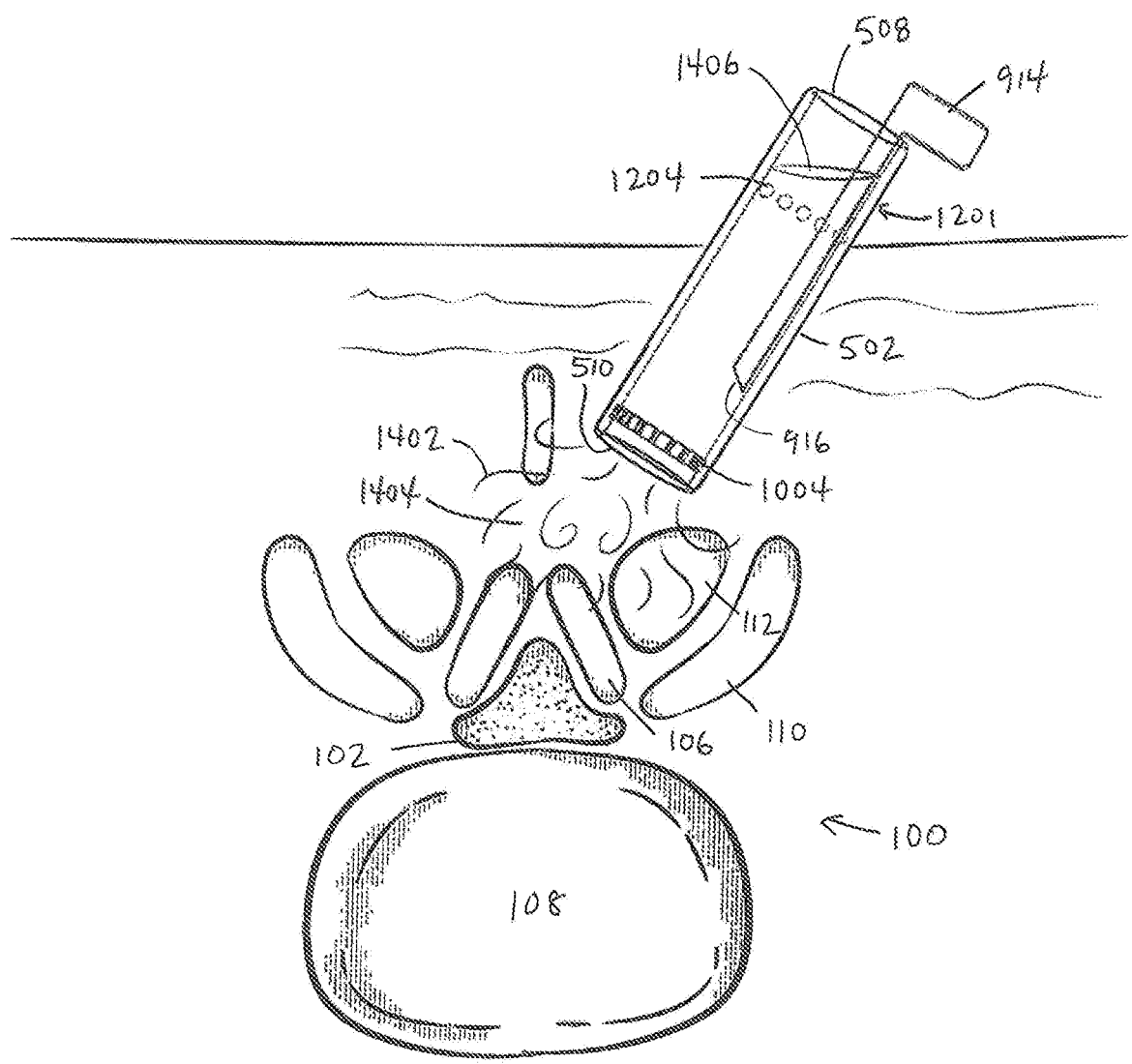
FIG. 14 is a schematic diagram of the retractor system of FIG. 12 positioned in a submerged surgical field adjacent to the lumbar spine portion of FIG. 1, wherein the fluid level within the retractor is proximal to the camera lens and slightly proximal to the level of the suction holes.

Referring now to FIG. 14, when both the distal irrigation system (e.g., 1004, 1206, 1210 and 1211) and proximal suction system (e.g., 1204, 1208, 1212 and 1213) are active, the irrigation fluid 1402 can flow from the distal end 510 of the retractor 1201, fill the surgical bed 1404, and fill the distal working end of the tubular retractor body 502 to a level (denoted 1406) proximal to the camera lens 916, until it nears the proximal end 508 of the retractor where the suction holes 1204 will remove excess fluid and any generated debris. FIG. 14 demonstrates the retractor 1201 in place with a submerged surgical field and water level above the camera lens 916 to the level of the suction holes 1204.

The suction holes 1204 can prevent fluid 1402 from rising beyond the proximal end 508 of the tube body 502 and out of the patient and surgical field 1404, thereby maintaining a dry environment outside the tubular retractor. The distal fluid irrigation source 1004 and proximal suction holes 1204 can also serve to remove debris by drawing it out of the surgical bed 1404, beyond the camera lens 916, and to the proximal suction tubes 1212 and 1213 for removal from the surgical field, thus maintaining a clear fluid working environment to facilitate improved visualization.

This combination of features will provide the option of either a dry or fluid submerged working environment. If the procedure calls for implantation of instrumentation (such as a fusion device), bone graft material, or other biologic material, a dry environment may be necessary to place and maintain material in its intended position. However, other portions of a procedure which may generate debris, such a burring of bone during laminotomy, may be better achieved while the surgical field is submerged in a fluid environment. Using the disclosed retractors, e.g., retractor 1201, the operator can perform certain portions of the procedure, such as decompression and laminotomy, in a fluid environment by continuously activating both the distal irrigation system (e.g., through irrigation holes 1004) and proximal suction system (e.g., through suction holes 1204), and then elect to use only intermittent distal irrigation as needed to maintain a dry environment during the insertion of implants or biologic material. In order to free the operator's hands further, the irrigation system and suction system in the retractor 1201 can be differentially controlled by foot pedals (not shown) so that irrigation and suction can be manually controlled intermittently or both turned on constantly to maintain a fluid submerged environment.

Figure 15:
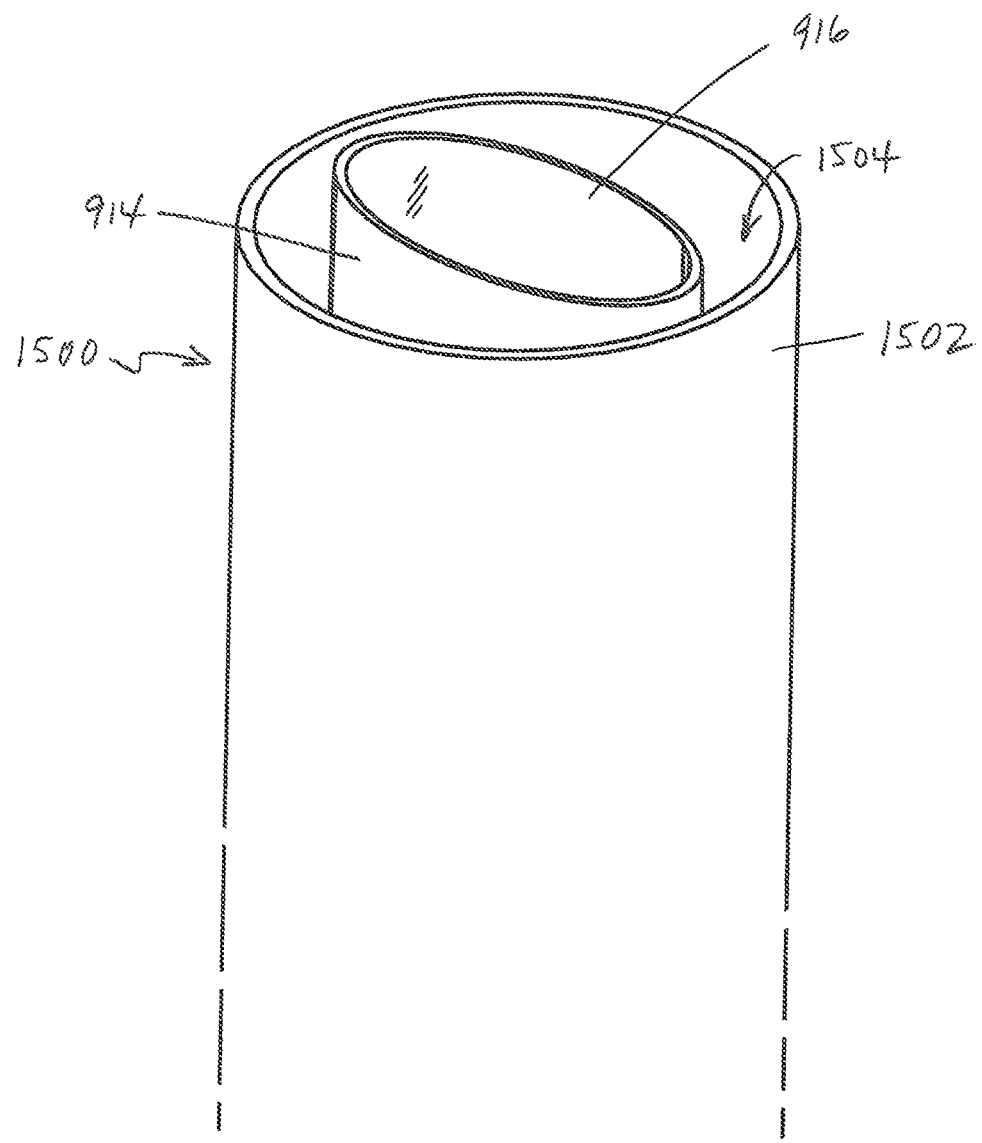
FIG. 15 is an enlarged partial perspective view of the distal end of an exemplary camera assembly with suction in accordance with another aspect.

Referring now to FIG. 15, there is illustrated an alternative camera assembly with suction 1500 according to another aspect. During use of the retractor 1201 with both irrigation and suction systems, the distal working end of the scope (i.e., camera 914) with the lens 916 can move intermittently between a dry environment and a wet environment during the procedure. Camera lenses that go from a fluid to dry environment often get fluid residue on the lens 916 that can obscure the view. To minimize this problem, in some embodiments the camera assembly with suction 1500 can include an outer housing sheath 1502 that surrounds at least the distal end of the camera 914, thereby forming an annular passage 1504 around the lens 916. The annular passage 1504 can be connected to suction to provide a self-cleaning mechanism by constantly removing fluid residue from the distal end of the camera scope lens 916. This will allow the operator to continue working uninterrupted when transitioning from wet to dry environment, rather than having to remove the endoscope and camera continuously for manual cleaning. The camera assembly with suction 1500 can be used for the camera 916 inserted in the passage 507 of a final retractor (e.g., retractor 1201), or as a stand-alone camera as further described below.

Figure 16:
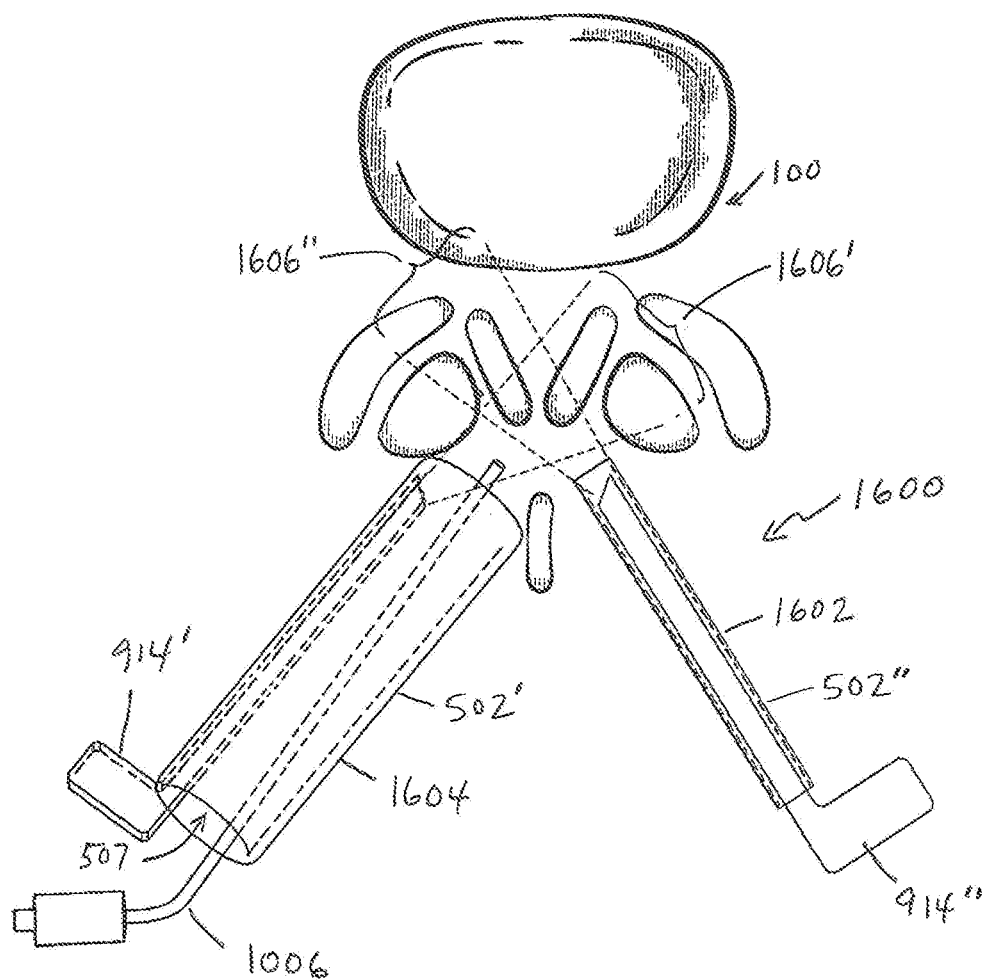
FIG. 16 is a schematic view of an exemplary multiple retractor system including a first tubular retractor and a second tubular retractor in accordance with another aspect positioned near the lumbar spine portion of FIG. 1, wherein the first tubular retractor has optional irrigation and/or suction systems, first camera and optional supplemental standalone suction tip and wherein the second tubular retractor has a reduced-diameter tubular body and second camera, and wherein the second tubular retractor is positioned on the contralateral side of the spine to allow for visualization of the lateral recess area on the side of the larger working channel retractor.

Referring now to FIG. 16, given the limitation of field of view of the ipsilateral lateral recess, a retractor system 1600 according to another aspect includes a second, smaller-diameter tubular retractor 1602 in addition to the main retractor 1604. The main retractor 1604 can be similar to retractors 500, 800, 900, 1001 and/or 1201 previously described (for purposes of illustration, some details of the retractor are omitted in FIG. 16), and can be equipped with a first camera 914' or first camera with suction assembly 1500' positioned inside the tubular body 502'. The second retractor 1602 can also be similar to retractors 500, 800, 900, 1001 and/or 1201, except having a smaller diameter for the tubular body 502" compared to the tubular body 502' of the main retractor 1604. The second retractor 1602 can be positioned on the contralateral side, which allows placement of a second camera 914" or second camera with suction assembly 1500 inside the tubular body 502" directed toward the contralateral side of the spine. In FIG. 16, the respective fields of view 1606' and 1606" of the cameras 914' and 914" are denoted by broken lines.

3) Navigated Microendoscopic Burr

Figure 17:
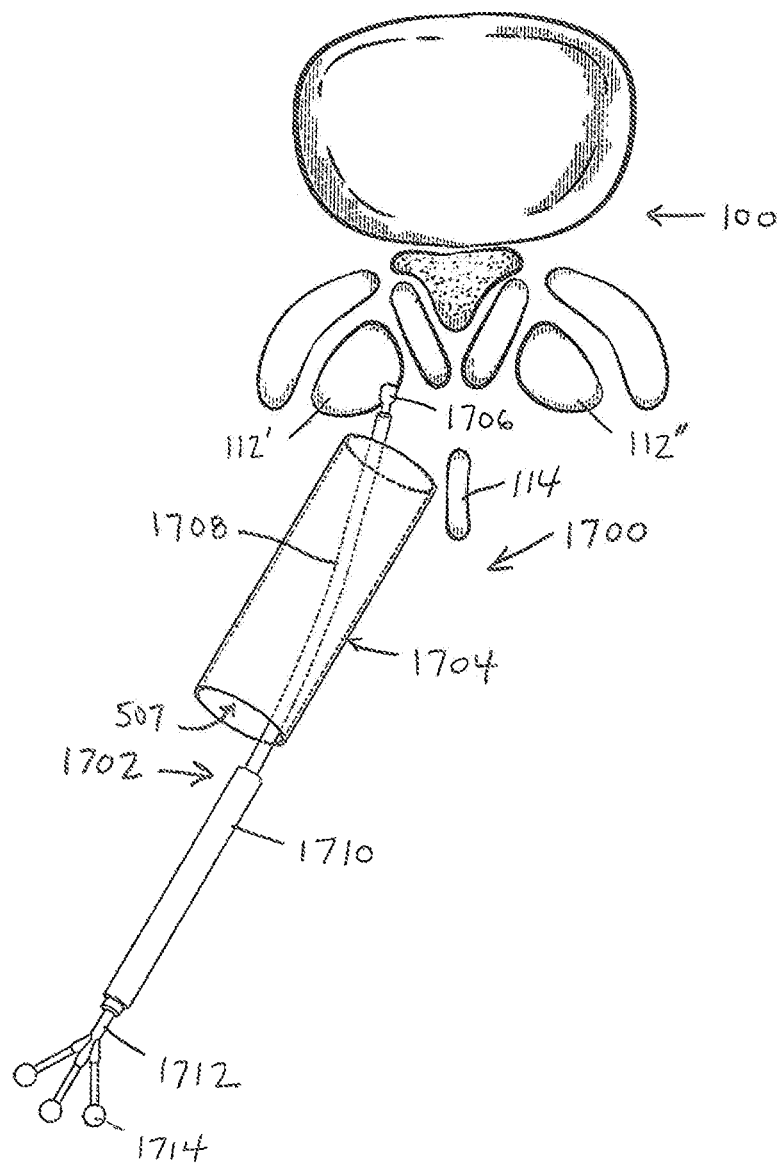
Figure 18:
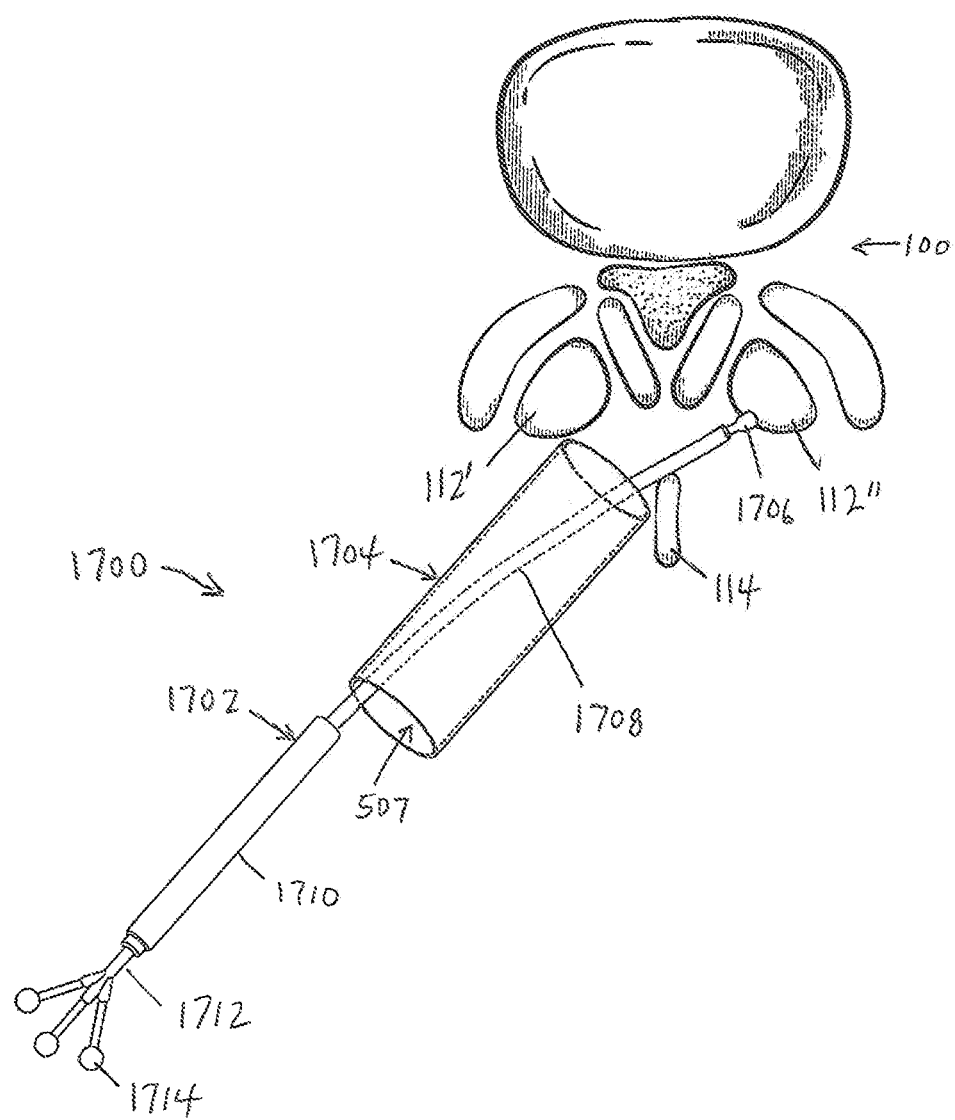
Figure 19:
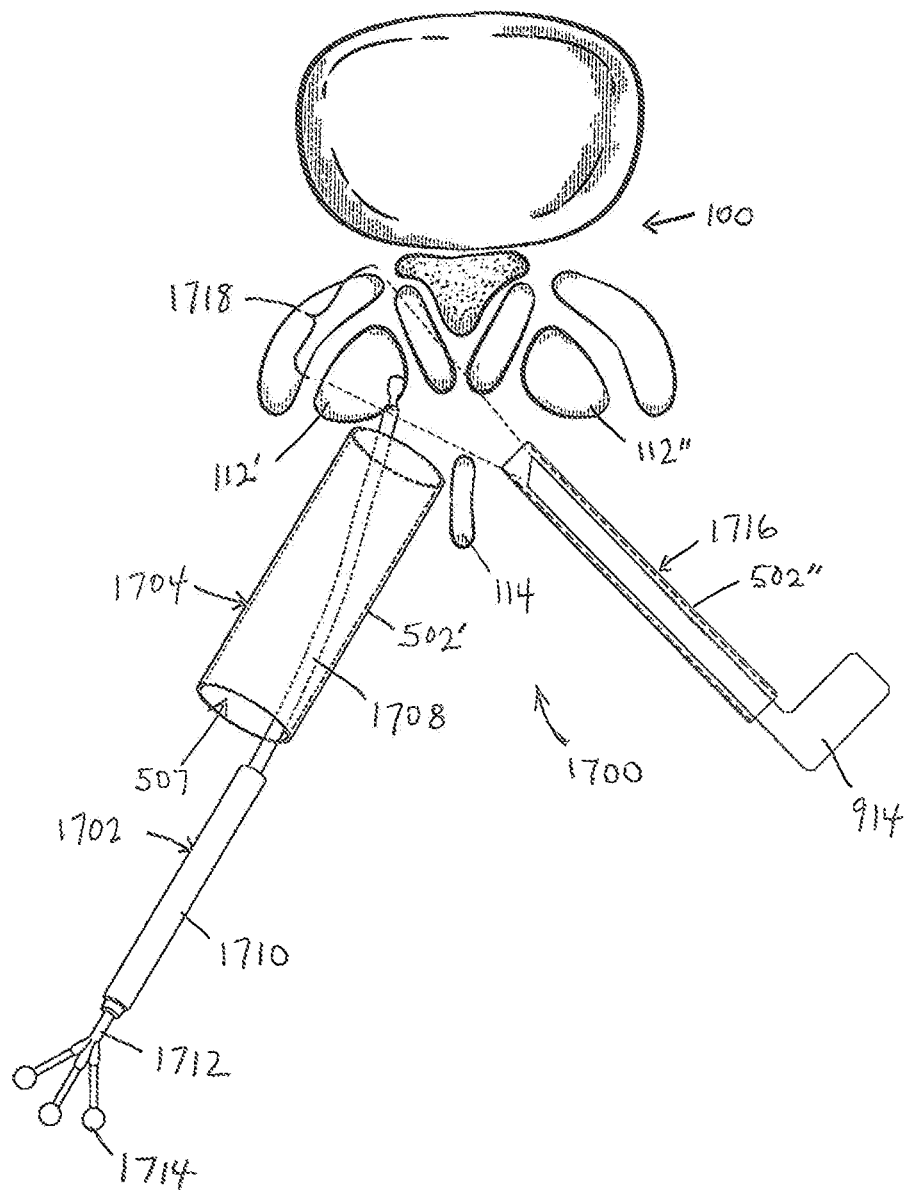
FIG. 19 is a schematic view of the retractor system of FIG. 17 further including a second retractor with camera placed on the contralateral side, allowing the surgeon to directly view the ipsilateral recess while utilizing the primary larger retractor as a working channel for instruments (i.e., a navigated burr is directed toward the operator through the working channel, performing the ipsilateral laminotomy, while under direct visualization from the contralaterally placed camera)

Referring now to FIGS. 17-19, there is illustrated a surgical instrumentation system 1700 including a navigated microendoscopic burr 1702, the distal end of which can be inserted through the interior passage of a tubular retractor 1704. A burr, e.g., burr 1702, is an essential component for bone removal. Some portions of bone removal, including the removal of a portion of the base of the spinous process 114 to allow for positioning of the tubular retractor 1704 more midline, is best achieved with a burr. Similarly, the undercutting of the contralateral lamina is also best performed with a burr. The burr 1702 can include a burr tip 1706 mounted in a tip holder 1708 extending from a handpiece 1710. The burr 1702 can further include a navigation marker 1712 connected to a proximal portion of the handpiece 1710. The tubular retractor 1704 can be similar to retractors 500, 800, 900, 1001 and/or 1201 previously described (for purposes of illustration, some details of the retractor are omitted in FIGS. 17-19). The navigation marker 1712 can be similar to navigation markers 306 and 506 previously described, and can include radio-opaque marker bodies 1714 similar to marker bodies 314 and 514. The navigation marker 1712 can be either permanently attached or removably attachable to the handpiece 1710. In either case, when attached, the marker bodies 1714 are positioned at a predetermined location relative to the burr tip 1706, thus, the marker bodies allow both the location and orientation of the burr tip 1706 to be determined and/or tracked via radio imaging.

As previously described, prior to bone removal and identification of the midline ligamentum raphe, there are limited anatomic landmarks that can be directly visualized to provide information about spatial relationships. Navigation of the burr 1702 with respect to multi-planar image reconstructions can allow the operator to identify the location of the burr tip 1706 on image reconstructions and thus direct the burr and bone removal in a manner which allows adequate bone removal for decompression of the neurologic elements, without compromising key stabilizing structures like the facet joint and the pars. This can help avoid the problem of iatrogenic instability after decompression surgery.

Referring now specifically to FIGS. 17 and 18, to allow the operator to maintain hold on the handpiece 1710 during use, in some embodiments the burr 1702 has a total working length, from distal end of the tip 1706 to the proximal end of the tip holder 1708, which is longer then the length of the tubular retractor 1704. The tip holder 1708 is preferably configured to be as small as possible with regard to circumference and diameter in order to minimize the area within the passage 507 of the tubular retractor 1704 it occupies while still maintaining stability of the burr tip 1706. Because the burr tip 1706 may need to remove bone on both the side ipsilateral and contralateral to the retractor 1704, in some embodiments the burr tip holder 1708 extending from the handpiece 1710 is configured, in an arc-shaped configuration (as illustrated) or an angled configuration (not shown) such that the burr tip can be placed in a position to work either toward or away from the operator by rotating the handpiece. For example, FIG. 17 illustrates the navigated burr 1702 rotated into a first position to decompress the ipsilateral side interior articular process 112', and FIG. 18 illustrates the navigated burr rotated into a second position to decompress the contralateral side interior articular process 112". As previously described, the tip holder portion 1708 of the burr 1702 has a predetermined configuration such that the tip 1706 will have a known position in space relative (in both position and orientation) to the tracking markers 1712 and 1714 attached to the burr, which will allow the tip 1706 to be accurately depicted on multi-planar image reconstructions.

Referring now to FIG. 19, in a further embodiment, the surgical instrumentation system 1700 can include a second tubular retractor 1716 to facilitate direct visualization of the decompression during certain parts of the procedure. The second tubular retractor 1716 can be similar to second retractor 1602, in other words, similar to previous retractors 500, 800, 900, 1001, 1201 and/or 1704, except having a smaller diameter for the tubular body 502" compared to the tubular body 502' of the main retractor, e.g., retractor 1704. In the illustrated embodiment of FIG. 19, the surgical instrumentation system 1700 includes the first retractor 1704 placed in the ipsilateral position for insertion and operation of the burr 1702, and the second tubular retractor 1716 with camera 914 placed in the contralateral position and oriented for direct visualization of the decompression on the ipsilateral side of the spine (the field of view for the camera 914 being denoted by dotted lines 1718).

4) Navigated Osteotomes

Figure 20:
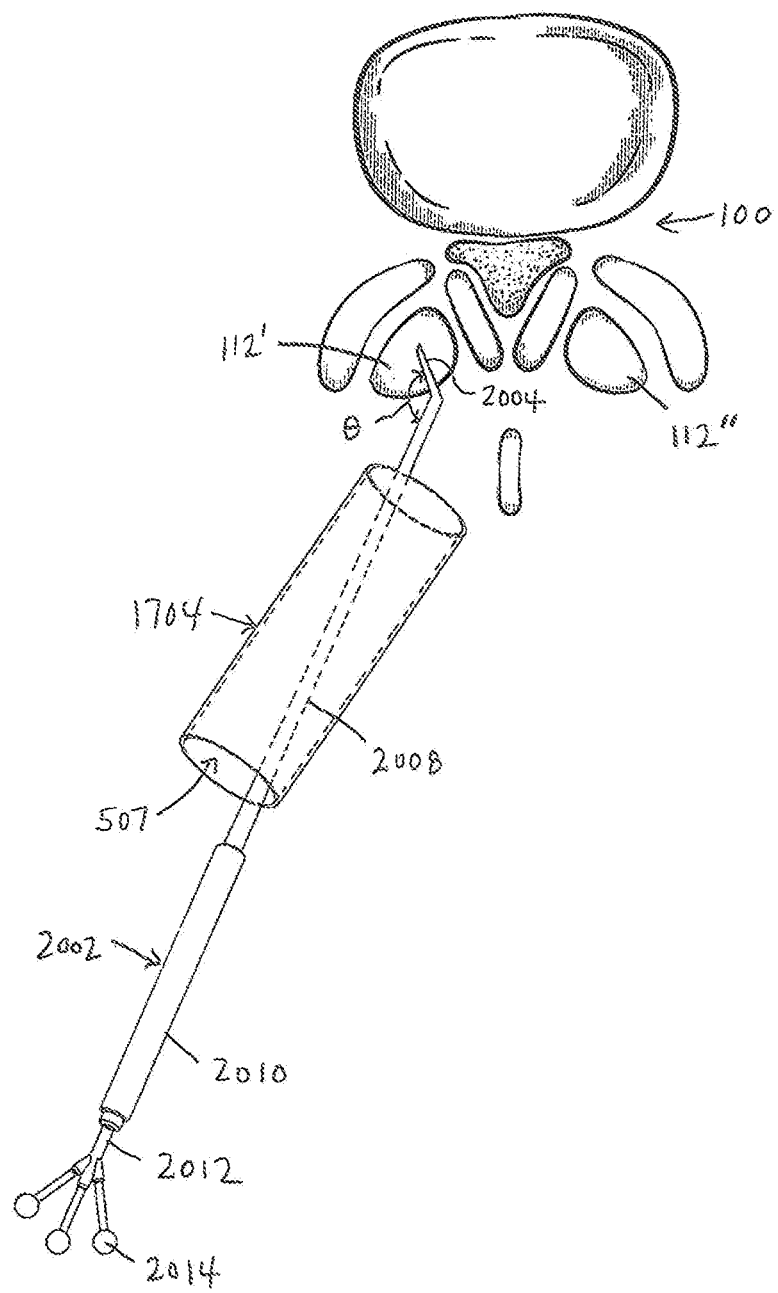
Figure 21:
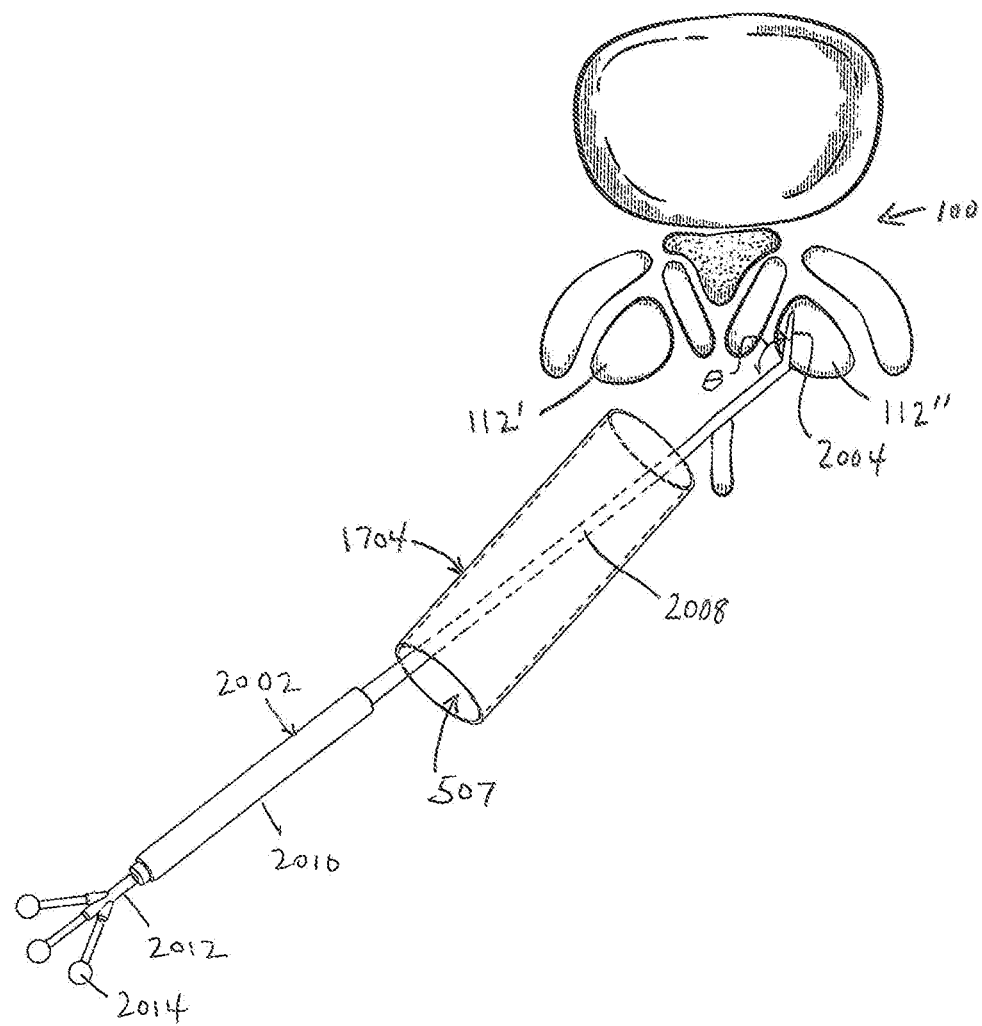

Referring now to FIGS. 20 and 21, there is illustrated a surgical instrumentation system 2000 including a navigated osteotome 2002. Osteotomes are sharp flat cutting tools which allow for removal of bone by creating a thin straight cut with the distal end. Osteotomes can be utilized to create initial bony cuts which define the borders of the bony decompression. The navigated osteotome 2002 includes a distal cutting portion 2004 (also called the distal end or working end) connected by an elongated shaft 2008 to a handle/handpiece 2010. The distal end 2004 can be inserted through the interior passage 507 of a tubular retractor, for example the retractor 1704 or any of the other retractors disclosed herein, to reach the site of the decompression.

In the context of microendoscopic decompression, where there is limited direct visualization, navigating the osteotome on multi-planar imaging and making initial bone cuts in this manner can define the lateral borders of the decompression and provide the operator with anatomic boundaries which can be clearly visualized. To facilitate such navigation, the navigated osteotome 2002 can further include a navigation marker 2012 connected to a proximal portion of the handpiece 2010. The navigation marker 2012 can be either permanently attached or removably attachable to the handpiece 2010. In either case, when attached, the marker bodies 2014 are positioned at a predetermined location relative to the distal portion 2004, thus, the marker bodies allow both the location and orientation of the sharp distal portion 2004 to be determined and/or tracked via radio imaging.

The shape of the osteotome 2002 can be important in defining the functional ability to make cuts in a particular desired direction, especially when the operator is working through the limitations of a tubular retractor, for example, the retractor 1704. In some cases, the osteotome cuts on the ipsilateral and contralateral sides will require different angulation of the osteotome 2002 in order to achieve the desired direction of the cut. Given that the operator is limited in the movement of the shaft 2008 and/or handle 2010 within the passage 507 of the tubular retractor 1704, in such cases the working end 2004 of the osteotome will need much variation in the angle of the osteotome blade relative to the shaft in order to achieve the necessary cut angles. Therefore, in some embodiments the distal working end 2004 of the osteotome 2002 is configured to extend from the shaft 2008 in an angled configuration such that the working end can be placed in a position to work either toward or away from the operator by changing the angle of the handpiece 2010. In other words, a first line along the center of the working end 2004 will form a configuration angle, denoted θ, with a second line along the center of the shaft 2008. In some embodiments, the navigated osteotome 2002 can have the configuration angle θ from 10 degrees to 80 degrees. In other embodiments, the navigated osteotome 2002 can have the configuration angle θ from 20 degrees to 60 degrees. In still other embodiments, the navigated osteotome 2002 can have the configuration angle θ from 15 degrees to 50 degrees. It will be understood that these angles θ are for exemplary osteotomes 2002, and are not limiting.

For example, FIG. 20 illustrates the navigated osteotome 2002 having configuration angle θ of about 45 degrees inserted through the retractor 1704 into a first position wherein the working end 2004 is at a first depth and a first working angle to decompress the ipsilateral side interior articular process 112'. FIG. 21 illustrates the navigated osteotome 2002 repositioned within the retractor 1704 into a second position wherein the working end is at a second depth and a second working angle to decompress the contralateral side interior articular process 112". These bone cuts could be made using navigation during the initial phase of the recess decompression in order to define the boundaries of the decompression. This will allow the operator to directly visualize the bony boundaries of the decompression.

It will be appreciated by those skilled in the art having the benefit of this disclosure that this instrumentation and surgical method for image-guided microendoscopic decompression provides navigated retractor systems with optional irrigation and/or suction systems, camera systems with optional suction systems for use with such retractor systems or standalone use, and navigated instruments including burrs and osteotomes for use with such retractor systems or standalone use. It should be understood that the drawings and detailed description herein are to be regarded in an illustrative rather than a restrictive manner, and are not intended to be limiting to the particular forms and examples disclosed. On the contrary, included are any further modifications, changes, rearrangements, substitutions, alternatives, design choices, and embodiments apparent to those of ordinary skill in the art, without departing from the spirit and scope hereof, as defined by the following claims. Thus, it is intended that the following claims be interpreted to embrace all such further modifications, changes, rearrangements, substitutions, alternatives, design choices, and embodiments.

What is claimed is:

1. Instrumentation for microendoscopic surgery comprising:
    a retractor having a tubular wall with an inner surface and an outer surface, the inner surface defining an interior passage extending through the retractor between a proximal end and a distal end;
    the tubular wall of the retractor including a fluid irrigation system having a plurality of irrigation outlet holes formed only in the inner surface of the tubular wall and disposed within the interior passage circumferentially around the interior passage near the distal end, an irrigation inlet formed in the outer surface of the tubular wall and positioned proximal to the irrigation outlet holes, and at least one irrigation channel formed within the tubular wall between the inner surface and the outer surface and fluidly connecting the irrigation inlet to the plurality of irrigation outlet holes;
    a camera including an imaging lens disposed within the interior passage of the retractor proximal to the irrigation holes, the imaging lens providing a field of view extending in a distal direction past the distal end of the retractor; and
    a multi-planar navigation marker mounted to the retractor in a first predetermined multi-planar spatial relation to the distal end of the retractor; and
    wherein the tubular wall of the retractor further comprises a fluid suction system having a plurality of suction inlet holes formed only in the inner surface of the tubular wall and disposed within the interior passage circumferentially around the interior passage at a position proximal to the irrigation outlet holes and to the camera imaging lens, a suction outlet formed in the outer surface of the tubular wall and disposed proximal to the suction inlet holes, and at least one suction channel formed between the inner surface and the outer surface of the tubular wall and fluidly connecting the suction outlet to the plurality of suction inlet holes.

2. The instrumentation according to claim 1, wherein the fluid irrigation system and the fluid suction system are fluidly isolated from one another to allow fluid to be added into the interior passage of the tubular retractor near the distal end with the fluid irrigation system while concurrently withdrawing fluid from the interior passage of the tubular retractor near the proximal end with the fluid suction system, and the fluid irrigation system and the fluid suction system can be differentially controlled intermittently or both turned on constantly to selectively create either a fluid submerged surgical field or a dry surgical field.

3. The instrumentation according to claim 1, wherein a portion of the tubular wall of the retractor excluding only the distal end is radiolucent.

4. The instrumentation according to claim 3, wherein the distal end of the tubular wall of the retractor is radiopaque.

5. The instrumentation according to claim 1, further comprising:
    a dilator having a body with a distal dilator tip; and
    a dilator multi-planar navigation marker mounted to the dilator in a second predetermined multi-planar spatial relation to the distal dilator tip.

6. The instrumentation according to claim 5, wherein the dilator multi-planar navigation marker is mounted removably to the dilator.

7. The instrumentation according to claim 1, wherein the distal end of the tubular wall of the retractor is configured with a beveled tip having a shortened medial side configured to facilitate placement against the spinolaminar junction.

8. The instrumentation according to claim 1, further comprising:
    a navigated microendoscopic burr having a cutting head, the burr being configured to be inserted through the interior passage of the retractor until the cutting head is disposed distally beyond the distal end of the tubular wall of the retractor; and
    wherein when the cutting head is disposed distally beyond the distal end of the tubular wall of the retractor, the cutting head is within the field of view of the imaging lens of the camera.

9. The instrumentation according to claim 1, further comprising:
a navigated osteotome having a cutting blade, the osteotome being configured to be inserted through the interior passage of the retractor until the blade is disposed distally beyond the distal end of the tubular wall of the retractor; and
wherein when the blade is disposed distally beyond the distal end of the tubular wall of the retractor, the blade is within the field of view of the imaging lens of the camera.

10. Instrumentation for microendoscopic surgery comprising:
a first retractor having a tubular wall including an inner surface and an outer surface, the inner surface defining an interior passage extending between a proximal end and a distal working end, the interior passage configured to accommodate the intermittent insertion of surgical instruments therethrough from the proximal end through the distal working end;
a multi-planar navigation marker mounted to the outer surface of the tubular wall, the multi-planar navigation marker including a plurality of spaced-apart, radiopaque marker bodies; and
wherein the multi-planar navigation marker is disposed at predetermined multi-planar spatial and rotational relation to the distal working end of the retractor, including during the absence of surgical instruments from the interior passage; and
wherein the tubular wall of the first retractor further comprises a fluid irrigation system including:
at least one irrigation outlet hole formed only on the inner surface of the tubular wall facing the interior passage;
at least one irrigation inlet hole formed only on the outer surface of the tubular wall and disposed proximally relative to the at least one irrigation outlet hole; and
a first fluid-tight passage disposed within the tubular wall of the retractor between the inner surface and the outer surface connecting between the at least one irrigation inlet hole and the at least one irrigation outlet hole for transporting fluid therebetween; and
the at least one irrigation inlet hole being connectable to a source of an irrigation fluid such that, when the at least one irrigation inlet hole is connected to the source of the irrigation fluid, the irrigation fluid flows through the first fluid-tight passage and into the interior passage from the at least one irrigation outlet hole, including during the absence of surgical instruments from the interior passage.

11. The instrumentation according to claim 10, wherein the first fluid-tight passage is formed within the tubular wall of the first retractor between the inner surface and the outer surface so as to be undetectable on an inner contour of the inner surface or on an outer contour of the outer surface.

12. The instrumentation according to claim 10, wherein the tubular wall of the first retractor further comprises a fluid suction system including:
at least one suction inlet hole formed only on the inner surface of the tubular wall facing the interior passage and disposed proximally relative to the at least one irrigation outlet hole;
at least one suction outlet hole formed on the outer surface of the tubular wall; and
a second fluid-tight passage disposed within the tubular wall of the retractor between the inner surface and the outer surface connecting between the at least one suction inlet hole and the at least one suction outlet hole for transporting fluid therebetween; and
wherein the first fluid-tight passage is fluidly isolated from the second fluid-tight passage; and
the at least one suction outlet hole being connectable to a source of suction such that, when the at least one suction outlet hole is connected to the source of suction, the irrigation fluid can flow into the at least one suction inlet hole.

13. The instrumentation according to claim 12, wherein the second fluid-tight passage is formed within the tubular wall of the first retractor between the inner surface and the outer surface so as to be undetectable on an inner contour of the inner surface or on an outer contour of the outer surface.

14. The instrumentation according to claim 12, further comprising:
a camera assembly including an elongated camera body and a lens disposed at a distal end of the camera body; and
wherein the elongated camera body is configured to be insertable through the proximal end of the first retractor and positionable in the passage of the retractor such that the lens is disposed distal to the at least one suction inlet hole and proximal to the at least one irrigation outlet hole.

15. The instrumentation according to claim 10, further comprising:
a second tubular retractor having a second tubular wall having an inner surface and an outer surface, the interior surface defining an interior passage extending between a proximal end and a distal working end;
wherein the tubular wall of the first retractor has a first diameter; and
wherein the second tubular wall of the second retractor has a second diameter that is smaller than the first diameter.

16. The instrumentation according to claim 15, wherein the second tubular retractor further comprises:
a second multi-planar navigation marker mounted to the outer surface of the second tubular wall, the second multi-planar navigation marker including a plurality of spaced-apart, radiopaque marker bodies; and
wherein the second multi-planar navigation marker is disposed at predetermined multi-planar spatial and rotational relation to the distal working end of the second retractor.

17. The instrumentation according to claim 10, further comprising:
a camera assembly including a lens and an outer housing sheath surrounding the distal end of the lens, thereby forming an annular space between the outer housing sheath and the camera lens;
wherein the outer housing sheath is separable from the tubular wall of the first retractor and is configured to be insertable through the proximal end of the first retractor and extend towards the distal working end of the first retractor; and
wherein the annular space is fluidly connectable to a suction source such that, when the annular space is connected to the suction source, any fluid is drawn off the lens into the annular space.

* * * * *